United States Patent [19]

Galle et al.

[11] Patent Number: 4,517,160

[45] Date of Patent: May 14, 1985

[54] AUTOMATIC ANALYZING APPARATUS

[75] Inventors: Kevin Galle, New City, N.Y.; Ryoichi Orimo, Ohme, Japan; Masahiko Sakurada, Machida, Japan; Taiichi Banno, Hachioji, Japan; Sugio Manabe, Kodaira, Japan

[73] Assignee: Olympus Optical Company Limited, Japan

[21] Appl. No.: 460,915

[22] Filed: Jan. 25, 1983

Related U.S. Application Data

[62] Division of Ser. No. 139,469, Apr. 11, 1980, abandoned.

[30] Foreign Application Priority Data

Apr. 14, 1979 [JP] Japan ................................. 54-44912

[51] Int. Cl.³ ............................................. G01N 35/04
[52] U.S. Cl. ...................................... 422/65; 422/63; 422/100; 422/102; 422/104
[58] Field of Search .............................. 422/63–67, 422/102, 104, 100; 73/864.21

[56] References Cited

U.S. PATENT DOCUMENTS

| Re. 31150 | 2/1983 | Ginsberg et al. | 422/64 |
|---|---|---|---|
| 2,604,249 | 7/1952 | Gorham | 422/64 |
| 3,605,010 | 9/1971 | Folus . | |
| 3,697,185 | 10/1972 | Kassel et al. . | |
| 3,754,466 | 8/1973 | Ritchie et al. . | |
| 3,897,216 | 7/1975 | Jones et al. | 422/104 |
| 3,969,079 | 7/1976 | Catarious et al. | 422/64 |
| 3,985,507 | 10/1976 | Litz et al. | 422/65 |
| 4,066,412 | 1/1978 | Johnson et al. . | |
| 4,076,503 | 2/1978 | Atwood et al. . | |
| 4,091,323 | 5/1978 | Landis . | |
| 4,113,437 | 9/1978 | Duff et al. | 422/64 |
| 4,115,861 | 9/1978 | Allington et al. | 422/67 |
| 4,131,420 | 12/1978 | Range . | |
| 4,141,954 | 2/1979 | Shigetomi . | |
| 4,152,075 | 5/1979 | Rellstob . | |
| 4,204,917 | 5/1980 | Yamamoto et al. . | |
| 4,228,831 | 10/1980 | Kerns . | |
| 4,234,540 | 11/1980 | Ginsberg et al. . | |
| 4,260,581 | 4/1981 | Sakurada . | |
| 4,276,258 | 6/1981 | Ginsberg et al. | 422/67 |
| 4,285,906 | 8/1981 | Meltzer et al. . | |
| 4,315,891 | 2/1982 | Sakurada . | |
| 4,325,910 | 4/1982 | Jordan | 422/65 |
| 4,338,279 | 7/1982 | Orimo et al. . | |

*Primary Examiner*—Michael S. Marcus
*Attorney, Agent, or Firm*—Parkhurst & Oliff

[57] ABSTRACT

An automatic analyzing apparatus for effecting chemical analyses for various sample liquids such as blood, urine, and the like, comprising a sample delivery pump for metering a sample liquid into a reaction cuvette, a reagent delivery pump for delivering to the reaction cuvette a given amount of a given reagent selected from a plurality of reagents contained in a reagent cassette, to form a test liquid, a feed mechanism for successively supplying reaction cuvettes along a circular reaction line, a plurality of photometering sections arranged along the reaction line for effecting a plurality of photometric and/or nephelometric and/or fluorometric measurements for each test liquid at different time instances to produce a plurality of photometric results, and circuitry for receiving the photometric results and selecting therefrom given quantitative analytical data of a given test item.

4 Claims, 56 Drawing Figures

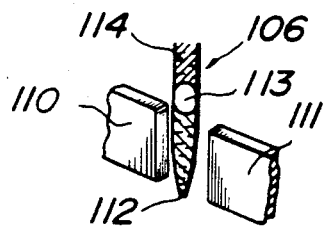
FIG.20A
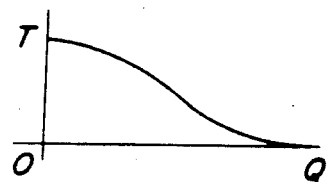
FIG.20B
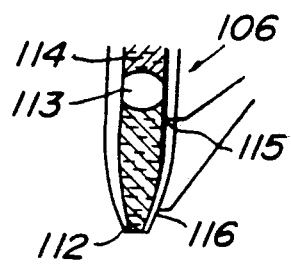
FIG.21A
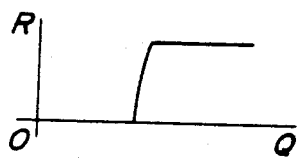
FIG.21B
FIG.22A
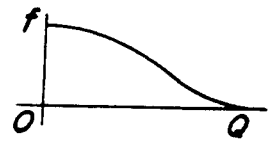
FIG.22B
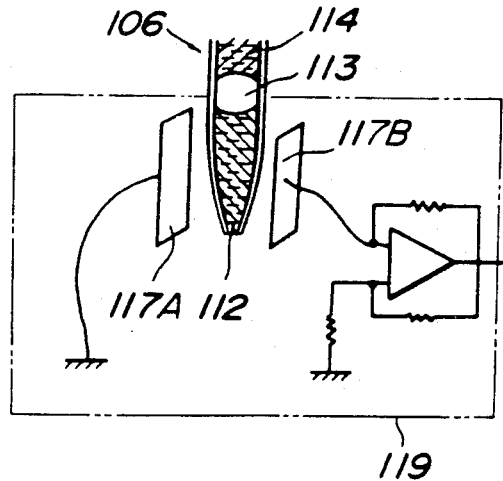

FIG. 33

| PRINT FIRMLY WITH BALL-POINT PEN | |
|---|---|
| OLYMPUS | |
| | PROFILE CHEMISTRY |
| | OLYMPUS |

| | MALE ☐ |
| | FEMALE ☐ |
| | ADULT ☐ |
| | JUV. ☐ |
| | INF. ☐ |
| | STAT ☐ |
| | ROUT ☐ |
| | TODAY ☐ |

53000/3152

| TESTS | EXPECTED VALUES | RESULTS | AF |
|---|---|---|---|
| ☐ Na+ mEq/L ☐ | | | |
| ☐ K+ mEq/L ☐ | | | |
| ☐ Cl− mEq/L ☐ | | | |
| ☐ Bicarb mEq/L ☐ | | | |
| ☐ UREA mg/dl ☐ | | | |
| ☐ GLU mg/dl ☐ | | | |
| ☐ TP gm/dl ☐ | | | |
| ☐ ALB gm/dl ☐ | | | |
| ☐ T.BILI mg/dl ☐ | | | |
| ☐ URIC mg/dl ☐ | | | |
| ☐ Ca++ mg/dl ☐ | | | |
| ☐ INPHOS mg/dl ☐ | | | |
| ☐ AST U/L ☐ | | | |
| ☐ LD U/L ☐ | | | |
| ☐ T.ALP U/L ☐ | | | |
| ☐ CHOL mg/dl ☐ | | | |
| ☐ TRIG mg/dl ☐ | | | |
| ☐ C.K. U/L ☐ | | | |
| ☐ CK-MB U/L ☐ | | | |
| ☐ D.BILI mg/dl ☐ | | | |
| ☐ CREAT mg/dl ☐ | | | |
| ☐ ACIDPHO. U/L ☐ | | | |
| ☐ GGT U/L ☐ | | | |
| ☐ T.IRON mg/dl ☐ | | | |
| ☐ LO-I U/L ☐ | | | |
| ☐ AM U/L ☐ | | | |

| PROFILE SELECTIONS | |
|---|---|
| ☐ COMPLETE PANEL (1-27) | |
| ☐ ROUTINE 6 (1-6) | |
| ☐ ROUTINE 12 (5-16) | |
| ☐ CARDIAC | FILL IN FOR TESTS REQUESTED |
| ☐ RENAL | |
| ☐ HEPATIC | |

NAME / AGE / HOSP. NO. / Location or Address

DEPARTMENT OF LABORATORIES HOSPITAL

TECHNOLOGIST: ___ DATE: ___ AM PM

R.N.

REMARKS

M.D.

DATE EXAM TO BE DONE / REQUESTED BY / DIAGNOSIS

LAB USE ONLY

CHEMISTRY

AUTOMATIC ANALYZING APPARATUS

This a division of application Ser. No. 139,469 filed Apr. 11, 1980, now abandoned.

BACKGROUND OF THE INVENTION

This invention relates to an automatic analyzing apparatus for automatically effecting chemical analyses of various sample fluids such as (but not limited to): cerebrospinal fluid, blood, urine, and the like.

Automatic chemistry analyzers can be roughly divided into two broad categories: continuous flow or discrete systems. Presently the majority of analyzer models employ the discrete approach to automation.

In a discrete system, each test is carried through the analytical process in its own dedicated (discrete) container or compartment. Current discrete analyzers can be further classified into two major sub-categories; sequential and centrifugal analyzers.

In sequential testers, all tests are performed sequentially, one after another, so that at any given point in time all tests in process are in a somewhat different stage of progress. In general, sample and reagent are metered into a vessel which is fed along a given path and the test liquids in each of the vessels are treated to each aspect of the analysis (reagent addition, mixing, quantitating, etc.) in sequence.

Centrifugal analyzers are also discrete but test liquids are processed in parallel to one another. All samples in process are in the same stage of analysis at the same time. In operation, samples and reagent are pre-measured and pre-loaded into appropriate compartments arranged about the circumference of a rotor disc, whereupon it is placed on a centrifuge and rotated at a high speed past a photometer device. Centrifugal force mixes all samples with reagent at the same time and hence each of the test liquids is in the same stage of analysis at any given point in time.

The majority of analyzers, regardless of the above mentioned categories, are capable of performing more than one type of test item. There are three broad categories of methods for providing for multi-test capability.

What shall hereinafter be referred to as Random Access Testers currently require individual test packs which are pre-packaged with the appropriate reagents required to perform one test of a given test type. These test packs are loaded into the instrument system according to the analyst's needs, charged with a sample liquid, and processed in a discrete manner. Random access testers offer great convenience and flexibility but currently available embodiments have low productivities when compared with other means of providing multi-test item capability. In addition, the requirement for pre-packaged test packs makes operating costs much higher than the alternate methods.

Another means of performing a plurality of tests on each of a plurality of samples is sequentially by test-item batch. All samples are analyzed sequentially or centrifugally for a given test item. When all samples have been analyzed for a given test item, the system is changed over, or somehow modified, to perform a different test item and all appropriate samples are re-treated. When all samples have been processed for the required test items, the results of each samples' test items must be collated to allow including all of a given samples analytical results on a single report form for return to a physician, etc. Such systems are usually referred to as 'single channel' systems. Single channel systems are usually considered most appropriate for treating a batch or plurality of samples, as the effort required to change-over from one test item to another is generally neither convenient nor cost-effective to treat one sample for a plurality of test items. Additionally, at any given moment in time, only one test item is available for immediate use.

Simultaneous analyzers have a plurality of analytical channels which enable a plurality of test items to be performed simultaneously on each sample. Such systems are commonly referred to as 'multi channel' analyzers. Multi-channel analyzers do make more than one test item available at any given point in time, do eliminate the data collating task required of single channel analyzers and in general, do have higher productivities than single-channel analyzers by virtue of the fact that they are constructed as a plurality of single-channel analyzers combined into one device. This last feature is a drawback in that it makes the analyzer system complicated in construction, large in size, and generally, much higher in cost than single-channel discrete, continuous flow or centrifugal analyzers.

In the known analytical systems of the non-centrifugal type, photometric quantitation is carried out after some time period from the initiation of the test reaction, i.e. when the test liquid has traveled along the processing line by some given fixed distance. Therefore, the reaction time is fixed as a function of the length or circumference of the processing line, which may or may not be optimal with respect to a given test item and/or sample.

Additionally, sequntial testers have only one photometer position per channel, severely limiting the amount of photometric data which can be made available. No photometric data can be made avilable until a test liquid reaches the photometer station, typically, 8–10 (often 30) minutes from the time of mixing of sample with reagent. Once a test liquid reaches a photometer station, the amount of time which is devoted to photometric measurement essentially limits the speed of analysis of a given sequential tester, i.e. if 60 seconds is devoted to photometric quantitation, then the processing rate is limited to 60 tests per hour. This feature forces a trade-off between processing rate and photometric quantitation time especially for 'kinetic' test (ex. enzyme rate tests) which require photometric measurement over long periods of time in order to provide for best accuracy and precision of analysis.

SUMMARY OF THE INVENTION

The present invention has as its object to provide for an automatic analyzing apparatus which is so constructed that the above drawbacks can be avoided while insuring consistently reliable results.

According to the invention, an apparatus for effecting automatic analysis comprises means for successively feeding reaction vessels, each containing a respective test liquid to be analyzed, along a given reaction line;

means for delivering (a) given amount(s) or (a) given reagent(s), corresponding to a test item to be measured, into a reaction vessel on the reaction line to form a test liquid;

a plurality of photometering means arranged at different measuring positions distributed along the reaction line for effecting a plurality of photometric measurements for a respective test liquid in a vessel at different time instances;

means for receiving results of said plurality of photometric measurements and selecting therefrom given quantitative analytical data of a given test item for the test liquid in a reaction vessel; and means for discharging the test liquid out of the reaction vessel after the quantitative analysis for the given test item has been performed.

BRIEF DESCRIPTION OF THE DRAWINGS

FIGS. 20A and 20B are a perspective view and a graph, respectively, showing an embodiment of a liquid level detector of the reagent delivery mechanism and a relation between an amount of sucked liquid and a detection output, respectively;

FIGS. 21A and 21B are a cross-sectional view and a graph showing another embodiment of the liquid level detector;

FIGS. 22A and 22B show still another embodiment of the liquid level detector;

FIG. 33 is a plan view showing a format of a patient card for use in the patient data system;

DESCRIPTION OF THE PREFERRED EMBODIMENTS

Figure 1:
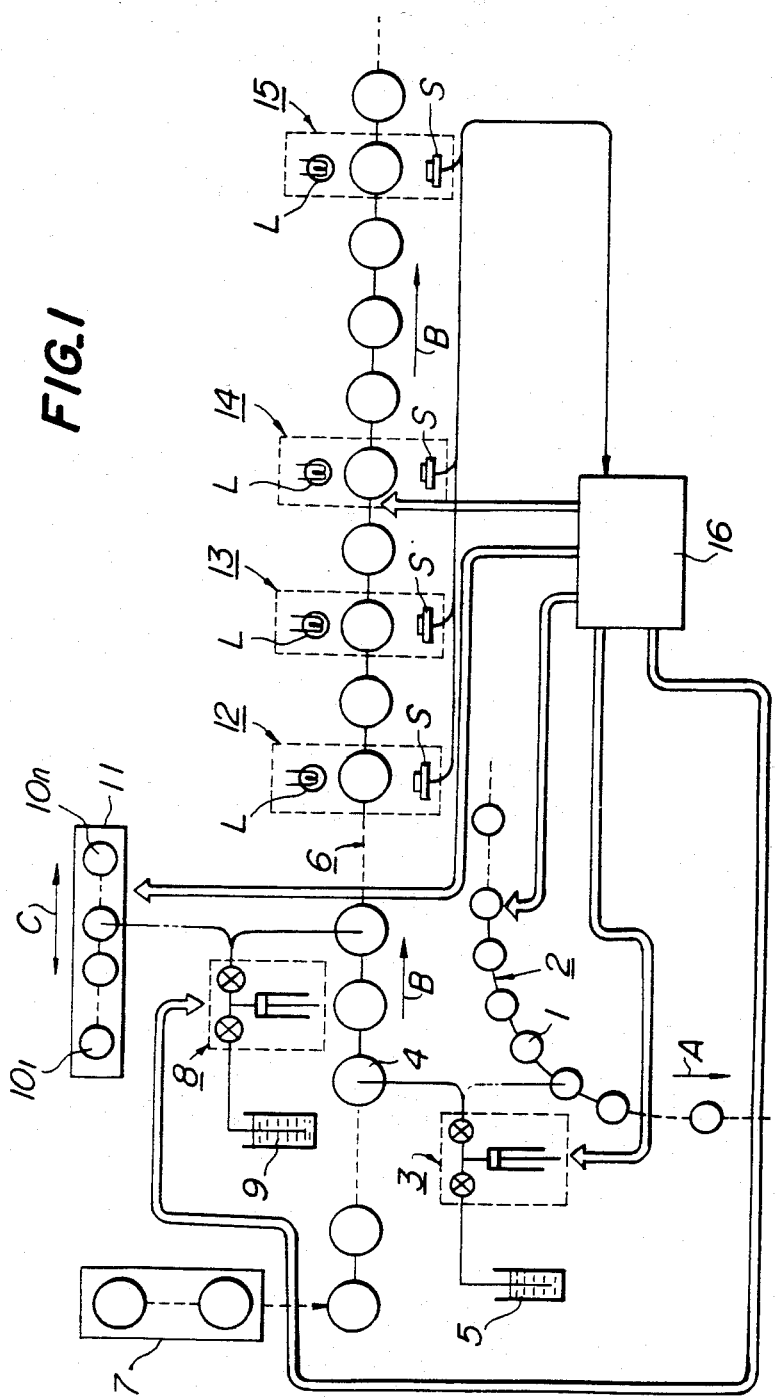
FIG. 1 is a schematic view illustrating a principal construction of an automatic analyzing apparatus according to the invention.

FIG. 1 is a schematic view illustrating a constructional principle of the automatic analyzing apparatus according to the invention. This apparatus can be classified as a discrete system adopting a batch process and belongs to a sequential multi system in which analyses for a plurality of test items can be effected continuously in succession. Sample vessels 1 are supported on a sample feed mechanism 2 and are intermittently fed in a direction shown by an arrow A. A given amount of sample liquid, contained in the successive sample vessels 1 are aspirated by a simple delivery mechanism 3 at a given position in accordance with test items to be analyzed and the given amount of sample liquid is supplied into cuvettes 4 together with a diluent 5 as required. The cuvettes 4 are supported by a curvette feed mechanism 6 and are intermittently fed along a reaction line B in a direction shown by an arrow B at a predetermined period, such as six seconds per step. New cuvettes 4 are successively supplied to the feed mechanism 6 from a cuvette-delivery mechanism 7. The cuvette 4 having the sample liquid delivered therein is advanced by several steps and arrives at a given position at which point a reagent, dependent on the test item to be measured, is delivered in the cuvette 4 together with a diluent 9 by means of a reagent-delivery mechanism 8. Reagents to be used for measurement are contained in reagent bottes $10_1$–$10_n$ which are supported on a reagent feed mechanism 11 movable in a reciprocal manner as shown by a double headed arrow C. A given reagent can be drawn by the delivery mechanism 8 from the bottle which is positioned at the given delivering position. The sample liquid and reagent can be sufficiently mixed by jetting the reagent into the cuvette 4 together with the diluent at a suitable flow rate. The cuvette 4 having had reagent and sample delivered thereto travels along the reaction line B. The test liquid in the cuvette is measured by photometers 12 to 15 each comprising a light source L and a light-receiving element S provided at positions separated from each other by distances equal to multiples of a traveling step of the cuvette. In this manner the reaction state of the test liquid in the cuvette 4 can be monitored as it progresses along the reaction line.

Figure 2:
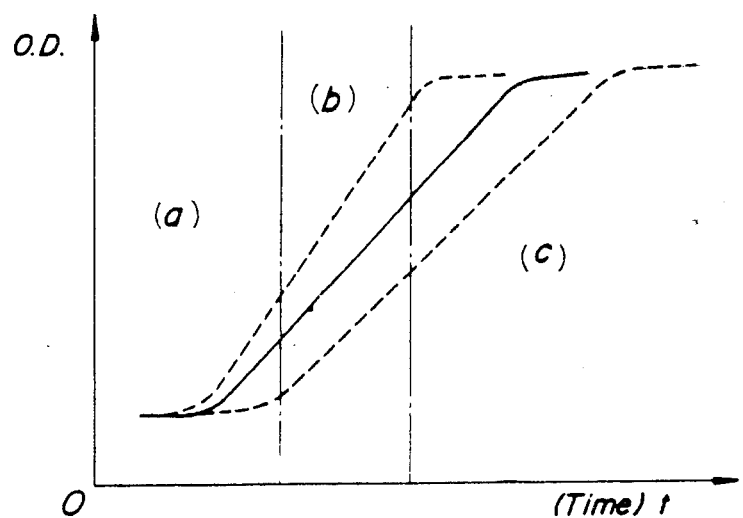
FIG. 2 is a graph showing typical reaction state of a test liquid.

Particularly in a measurement of enzymatic reactions, it is very imprtant to monitor the reaction over some extended period of time. That is to say, in the measurement of enzymatic reactions, it is impossible to obtain an accurate result unless a measurement is effected during the linear portion of an absorbance level-to-time characteristic curve. In FIG. 2, a typical reaction curve is shown and an absorption (O.D.) is plotted on the ordinate and time (t) measured from the addition of reagent, is plotted on the abscissa. In FIG. 2, a left-hand zone (a) represents the lag phase of reaction due to heating time of test liquid, mixing, etc., and a zone (b) denotes the linear phase in which the reaction rate measurement, i.e. kinetic reaction measurement, can be effected positively and accurately. Further a zone (c) represents an end point phase in which the reagent substrate or other given components in the test liquid have been exhausted. Measurement in the end point zone (c) results in erroneously low values when performing kinetic assays. The period of the linear phase (b) may be suitably changed by adjusting the substrate concentration, etc. and total volume of test liquid. This adjustment is effected in such a manner that the end of the lag phase (a) can be detected by the photomesters 12 to 15 (see FIG. 1) for almost all test liquids even if the test liquids have fast or slow reaction rate. Preferably the substrate concentration conditions, and total volume of test liquid are so adjusted that the variation in absorption can be observed after twelve seconds (corresponding to the position of photometer 12) from the mixing of reagent and sample for the test liquid having the slowest reaction rate and the linear phase (b) will last for one or two minutes or more for the normal test liquids. By such a measure, the lag phase of successively fed test liquids can be monitored in a substantially completed state by the photometers 12 to 14. It should be noted that the photometers 12 to 15 can monitor the linear phase (b) as well as the lag phase (a). That is to say, when the end of the lag phase is detected for a test liquid by one of the photometers 12 to 14, the measurement is effected for the relevant test liquid during the linear phase by means of a photometer which are situated beyond the above mentioned photmeter on the reaction line. After the measurement, the test liquid is discharged together with the cuvette 4.

The above mentioned sample feed mechanism 2, sample delivery mechanism 3, cuvette feed mechanism 6, reagent delivery mechanism 8, reagent feed mechanism 11 and the photometering sections can be controlled by a control device 16 including a computer on the basis of patient information introduced by an operator.

As described above, according to one aspect of the invention, the lag phase and linear phase are monitored at a number of positions on the reaction line to obtain a number of photometric data and then useful data are selectively derived from these data. By this measure it is possible to obtain the analytical data of high accuracy and reliability and thus a useful automatic analyzing apparatus having excellent and unique abilities can be realized.

Now, embodiments of the apparatus according to the invention will be explained.

Figure 3:
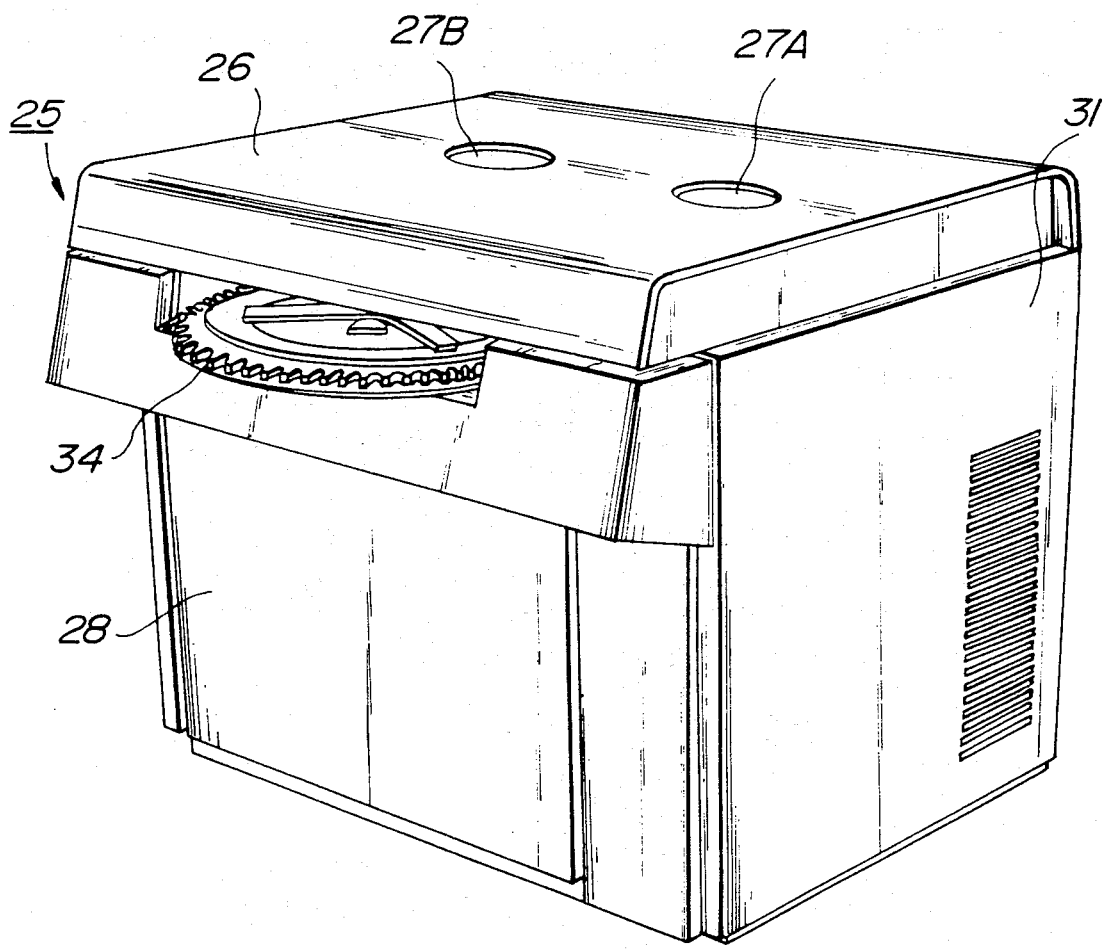
FIGS. 3 and 4 are perspective views illustrating an embodiment of the automatic analyzing apparatus of the invention.
Figure 4:
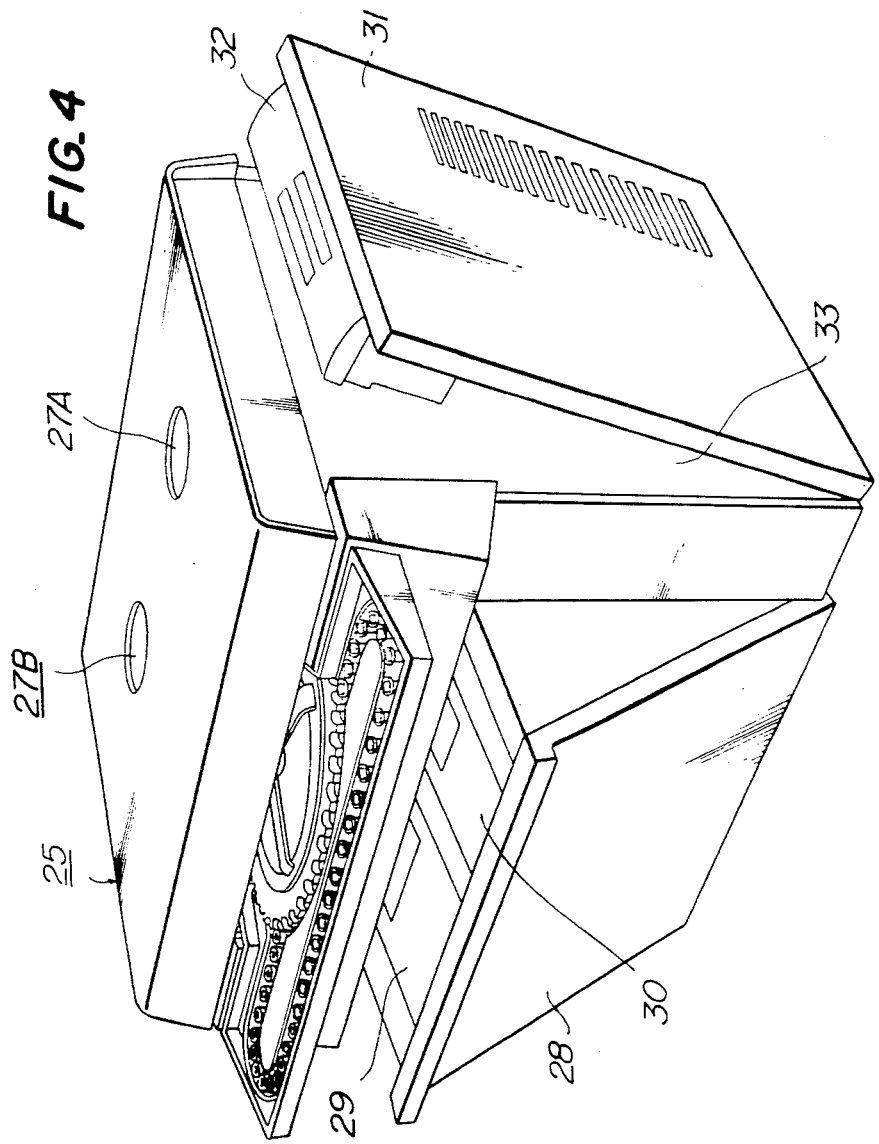

FIGS. 3 and 4 are perspective views illustrating an outer appearance of the automatic analyzing apparatus according to the invention. A main body 25 includes a cover 26 hinged at the rear to provide access to internal components. In the cover 26 are formed openings 27 for dissipating heat produced by light sources of photoelectric colorimeters. A front plate 28 is secured to the main body 25 in such a manner that the front plate can be opened to provide access. A cuvette container 29 for storing waste cuvettes and a waste liquid container 30 for storing waste liquid are detachably secured to the front plate 28. A right-hand side plate 31 is hinged to the main body 25 at the bottom side and a cassette holder 32 for supporting a detachable reagent cassette for holding various reagent bottles necessary for given analyses is provided on the side plate 31. A portion for fitting the cassette holder 32 defined by the right hand side plate 31 forms a refrigerator 33.

A sample liquid feed mechanism 34 is affixed to the main body 25 at its front portion. This mechanism comprises a rotating gear-like turntable which can be detachably installed in the apparatus when the cover 26 is opened. As shown in FIG. 4, a chain may be engaged with the turntable so as to feed the sample cups held by the chain. This chain may be selectively used, depending upon the number of test bodies to be analyzed.

Figure 5:
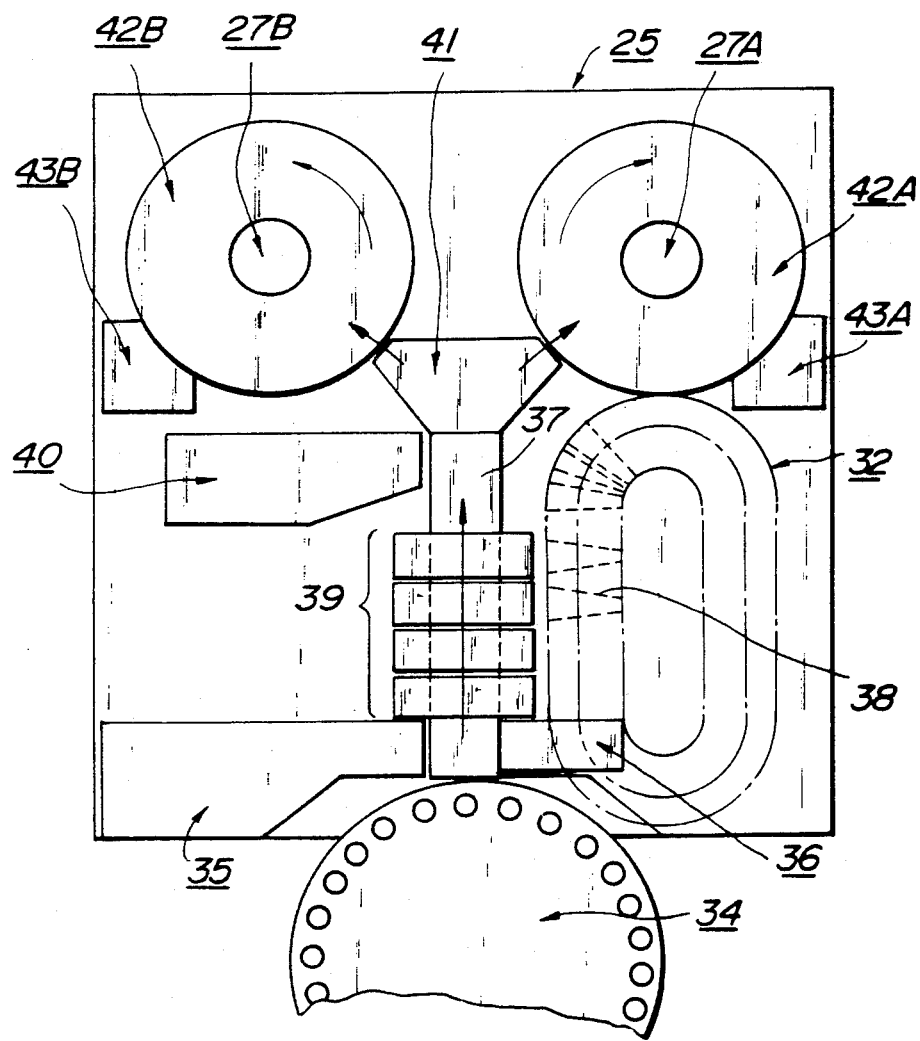
FIG. 5 is a schematic plan view showing an arrangement of various portions of the apparatus shown in FIGS. 3 and 4.

FIG. 5 is a schematic view illustrating an arrangement of various portions of the apparatus with the top cover 26 removed. The sample cups are fed successively by the feed mechanism 34 to a given aspiration position. The cuvettes are fed one by one by a cuvette supply mechanism 35 through a position near the sample aspiration position. A given amount of sample from the sample cup is supplied to the cuvette by a pump 36. While the cuvette is fed to a photo-metric position by a cuvette feed mechanism 37, a given amount of a suitable reagent is supplied to the cuvette from a reagent bottle 38 in the reagent cassette 32 by means of a reagent dispenser 39. A plurality of reagent bottles 38 are arranged in the cassette 32 along an endless path and any desired bottle 38 can be indexed at a position for aspirating the reagent therein by the dispenser 39. As will be explained later in detail, an ion sensor 40 is arranged along the cuvette feed mechanism 37 to measure concentrations of ions in the test liquid. At the end of the cuvette feed mechanism 37 a distributing mechanism 41 is arranged for continuously delivering successive cuvettes into right and left photometering sections 42A and 42b alternately. These photometering sections are communicated with the openings 27A and 27B, respectively formed in the cover 26. After the measurement in the sections 42A, 42B, the cuvette and its container are discharged at stations 43A and 43B.

When two photometering assembles 42 are provided even if the cuvettes are successively fed every six seconds by means of the feed mechanism 37, each test liquid can be measured for twelve seconds at each photometer position by either one of the photometering sections and thus, the time available for measurement can be increased. Further, even if one of the photometering assemblies becomes inoperative, the analyzing operation can be carried out.

Figure 6:
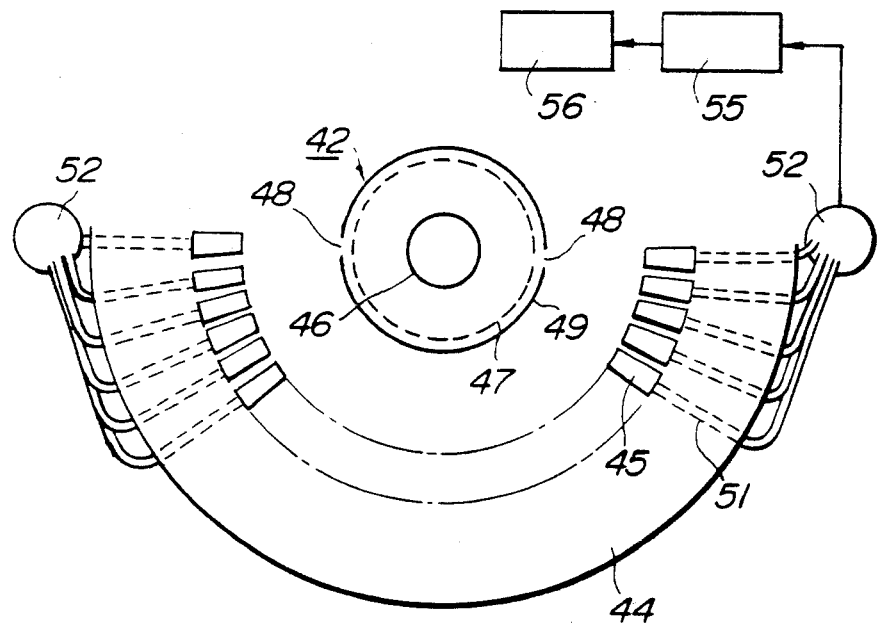
FIG. 6 is a plan view showing a photometering section of the apparatus of FIG. 5.
Figure 7:
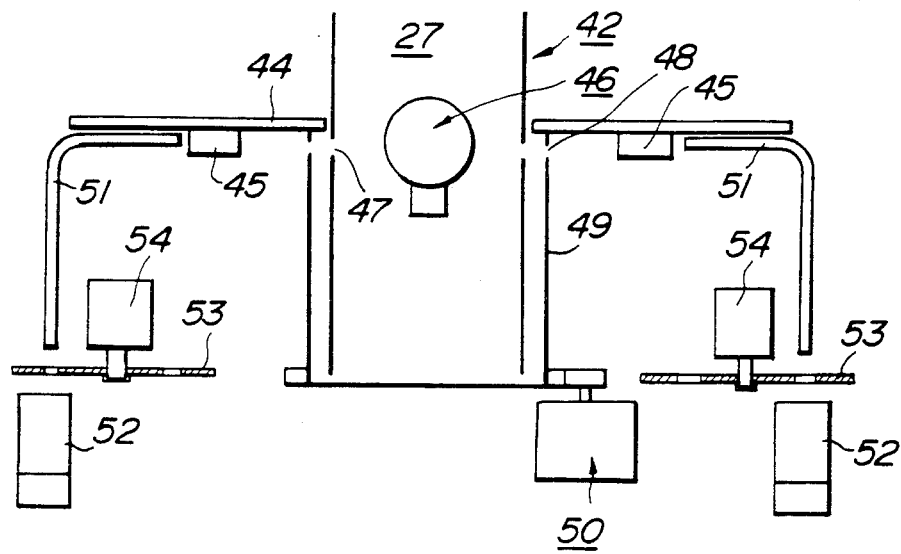
FIG. 7 is a schematic cross-sectional view showing the photometering section.
Figure 8:
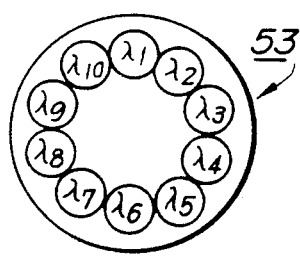
FIG. 8 is a plan view showing a rotary filter unit illustrated in FIGS. 6 and 7.

Next, a detailed construction of the photometering section will be explained. As illustrated in FIGS. 6 and 7 the photometering section 42 comprises a disc-shaped turntable 44 surrounding a chimney 27. A plurality of cuvettes are arranged along the periphery of the turntable 44. These cuvettes can be indexed past a number of photometering positions. The cuvette 45 is made at least partially of transparent material. A single light source 46 is arranged in the chimney 27 and a number of apertures 47 are formed in a cylindrical body defining the chimney 27 at positions corresponding to a number of photometering positions. These apertures are situated at the same vertical level as the light source 46. Around the cylinder forming the chimney 27 is rotatably arranged a drum 49 having formed a pair of slits 48 therein at the same level as the apertures 47. The drum 49 is rotated by a motor 50 at a high speed. There are further arranged a number of optical fibers 51 each having one end secured at a respective photometering position so as to receive a light emitted from the light source 46 through the aperture 47 and the slit 48 and transmitted through the cuvette 45. The other ends of these respective fibers are collected at one or two positions and are faced to photo detectors 52 comprising a photomultiplier tube or similar device. Between the collected ends of the fibers 51 and the photo detector 52 is arranged a rotary filter unit 53. As shown in FIG. 8, the rotary filter unit 53 comprises a plurality of filters $\lambda_1$ to $\lambda_{10}$ having different transmitting wavelengths and is rotated by a motor 54 to index a desired one into the light path between the distal end of the optical fibers 51 and the photomultiplier tube 52 or similar device. Output signals from the photo detectors 52 are supplied through an A/D converter 55 to a computer 56 provided in the control device 16.

In FIG. 6, it is assumed that the turntable 44 supports, for example thirty cuvettes 45 which are advanced at an interval of, for instance ten seconds, and the filter unit 53 is rotated by one revolution during these ten seconds. Then, each of the filter elements $\lambda_1$ to $\lambda_{10}$ passes through the light path reaching the photo detector 52 for about one second. During this one second, the drum 49 having formed the slits 48 therein is rotated by one turn. In this manner, absorption data for all wavelengths can be obtained at each photometering position. From these absorption data are selected desired data corresponding to a given wavelength or wavelengths which are determined by the test item, and the selected data are converted into digital values which are then stored in the computer 56. In this manner, for each test liquid in each cuvette on the turntable, the reaction data can be obtained from all photometering positions every ten seconds. Hence, absorbance data for any given test liquid in any given cuvette can be made available at any or all available wavelengths every ten seconds for as long as the cuvette and test liquid remains on the turntable. In the computer, the linear phase when pertinent, can be determined from this data, and thus the kinetic reaction data, if necessary, can be obtained accurately.

Figure 9A:
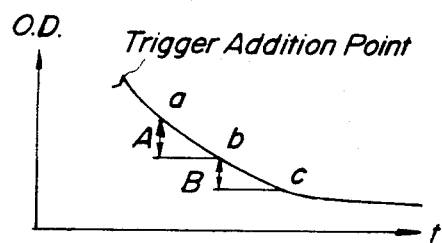
FIGS. 9A and 9B are graphs showing reaction curves.
Figure 9B:
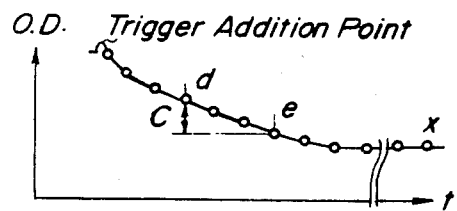

As shown in FIG. 9A, the linear phase can be determined at a section near a trigger addition point and having a small value of $|A-B|$. In order to obtain a reaction curve shown in FIG. 9B, it is necessary to compensate for differences in outputs from the photometering positions. To this end, prior to the measurement, a calibrating cuvette having highly accurate optical length is set in the apparatus and absorption values of this cuvette for all wavelengths are measured at all photometering positions and are stored in the computer. During the measurement, the stored absorption values are subtracted from detected values. In this manner, the reaction curve illustrated in FIG. 9B can be obtained.

By increasing the rotation speeds of the rotary filter unit 53 and the slit drum 49, a corresponding increase in data may be obtained from each measuring position.

Figure 10:
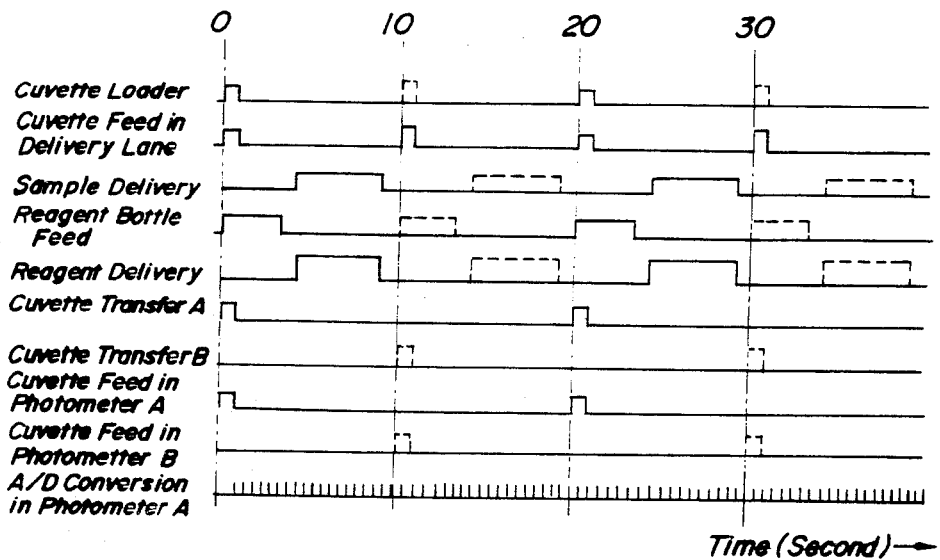
FIG. 10 is a chart for explaining an operation of the apparatus according to the invention.

FIG. 10 is a chart showing the operation of the apparatus according to the invention.

While FIGS. 6 and 7 show two sets of the slit, filter assemblies, and photo detectors, any number of such optical channels may be provided.

It should be noted that since in this embodiment use is made of sequential multi-test mode, it is, of course possible to measure continuously a plurality of test items for each sample as desired by the operator, and supplied to the computer-control device via keyboard, cards or other commonly used computer input devices, etc.

It should be noted that this embodiment offers an operator a number of choices which heretofore would require a sacrifice in productivity and/or convenience to obtain the desired combination of data gathering modes and/or capabilities as follows:

A. Monitoring the change in absorbance of a test liquid over time with capabilities for selectively determining the linear phase of the reaction.

B. Performing such monitoring as in 'A.' above at two or more wavelengths.

C. Gathering data for test liquids at only one or two points in time (herein referred to as end-point assays) at one more wavelengths when such desired test liquids are randomly interspersed on the turntable with test liquids requiring data gathering modes as in 'A.' or 'B.' above.

D. Conversely, test liquids requiring data gathering modes as in 'A.' or 'B.' above can be randomly interspersed on the turntable with end point assays as in 'C.' above.

E. It is further possible to effect continuously a single test item for all samples utilizing any or all of data modes 'A.' through 'C.' above or;

F. To treat a plurality of samples to a plurality of test items utilizing any or all of the data acquisition modes as in 'A.' through 'C.' above.

The apparatus of this embodiment further includes the ability for automatic calibration. This can be effected by setting a standard sample to the sample feed mechanism 34 during a stand-by condition. Then, the apparatus automatically operates at every constant time period and the standard sample is delivered into the cuvette 45 on the cuvette feed mechanism 37 and the automatic calibration is effected in a usual manner to compensate for drifts of the apparatus such as variation in brightness of the light source 46, etc.

This automatic calibration ability allows the instrument to be used at any time of day or night with complete confidence that the calibration routine is properly performed regardless of the relative expertise or attention of the operator.

The control of operation of various portions, the inputting operation of patient or sample information, and the calculation of the analyzed results can be effected by a control device (not shown) including one or more computers.

Figure 11:
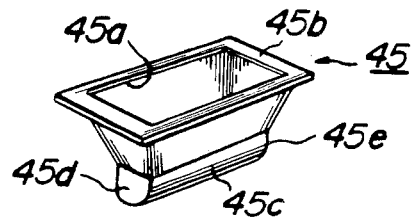
FIG. 11 is a perspective view showing an embodiment of a cuvette for use in the apparatus according to the invention.

FIG. 11 is a perspective view illustrating an embodiment of the cuvette 45. The cuvette 45 of this embodiment comprises a rectangular opening 45a and a supporting flange 45b provided at the periphery of opening. The opening is connected to a bottom portion 45c by a tapered side wall narrowing towards the bottom portion. The bottom portion 45c is formed as a semicylindrical shape and has measuring windows 45d at both ends, when viewed in its axial direction, through which windows the test liquid in the cuvette is optically measured.

Figure 12A:
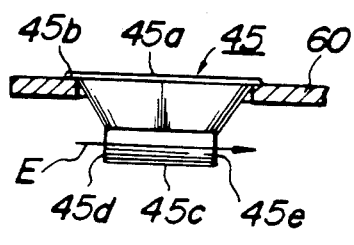
FIGS. 12A and 12B are side views illustrating a manner of holding the cuvette of FIG. 11.
Figure 12B:
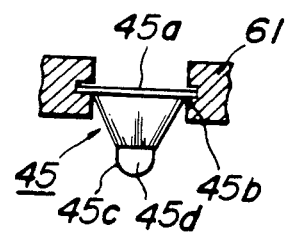

According to the above mentioned construction of cuvette 45, since the opening 45a (receiving port) is wide, it is possible to easily deliver the sample and reagent without sputtering them externally. Further, the amount of the test liquid is sufficient to fill the semicylindrical bottom portion 45c, and thus the analysis can be effected with very small amounts of the sample and reagent. Moreover, since a measurement axis extends in a longitudinal direction of the cuvette and thus is sufficiently long, it is possible to carry out the analysis with very high sensitivity. Since the side wall is tapered from the opening 45a to the bottom 45c, and the flange 45b is provided around the opening, the cuvette may be simply secured to the cuvette feed mechanism 37 in a manner shown in FIGS. 12A and 12B. That is, the flange 45b may be placed on a holding member 60 as illustrated in FIG. 12A or may be detachably inserted into recesses formed in a holding member 61 as depicted in FIG. 12B. In this manner, the cuvette 45 may be simply supported by the holding member without making the measuring windows 45d in contact with the holding member 60 or 61, and thus the measuring windows can be protected against injury. In FIG. 12A, an arrow E denotes the measuring optical axis. Further, the cuvette 45 may be formed by molding of transparent material, and thus its mechanical strength can be made high.

Next, the sample and reagent delivery mechanisms will be explained. Since these mechanisms can be constructed substantially similarly to each other, only the reagent delivery mechanism will be explained.

Figure 13:
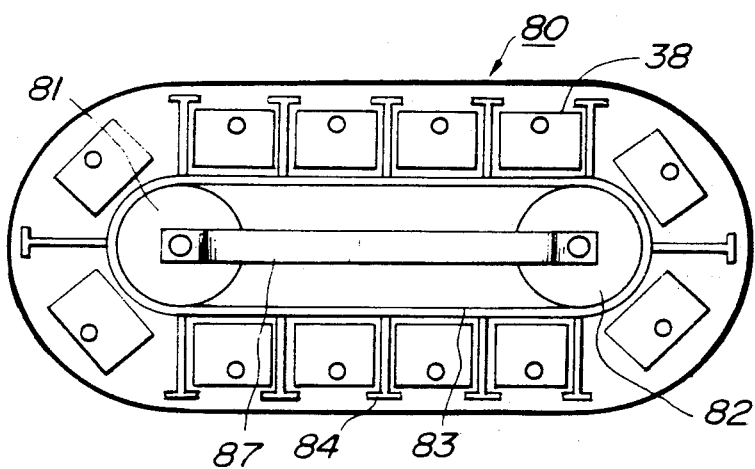
FIG. 13 is a plan view showing an embodiment of a reagent cassette.
Figure 14:
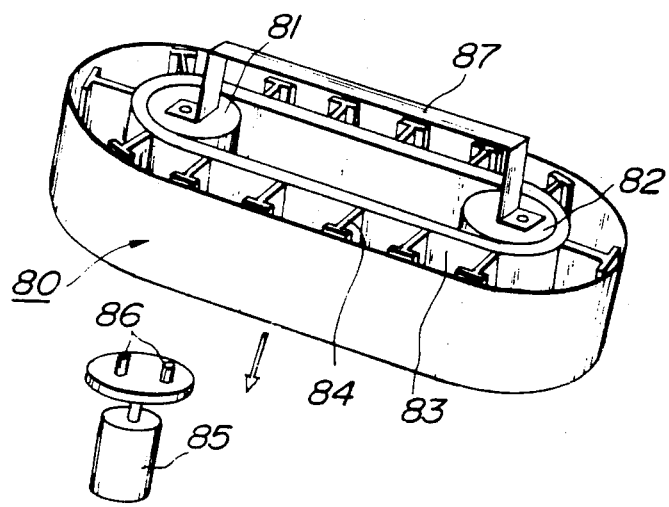
FIG. 14 is a perspective view illustrating the reagent cassette.

As illustrated in FIG. 5 in this embodiment, a plurality of reagent bottles 38 are arranged in the reagent cassette along an endless path. That is to say, as shown in FIGS. 13 and 14, the cassette comprises an elliptic outer frame 80 in which are arranged rotatably a pair of pulleys 81 and 82. An endless belt 83, preferably a timing belt, is arranged between these pulleys 81 and 82. A plurality of partitions 84 are integrally formed with the belt. The reagent bottle 38 is removably inserted into a space formed by adjacent partitions and the outer frame 80. One of the pulleys 81 has formed in its bottom surface, recesses which engage detachably with projections 86 formed on an output shaft of a stepping motor 85 secured to the main body 25. The stepping motor 85 may be driven in either a forward and/or backward direction as determined by means of an externally supplied signal. A handle 87 is secured to stationary shafts of the pulleys 81 and 82 so that the cassette can be easily set into, or taken out of, the holder 32.

In order to maximize the operational efficiency of the analyzing apparatus in which several reagents selected from a number of reagents, are delivered by a single delivery pump, it is preferable to effect the delifery of reagents in such an order that the total traveling distance of the cassette is minimized. For this purpose, the stepping motor 85 for transporting the reagent bottles 38 is of a reversible type.

Figure 15:
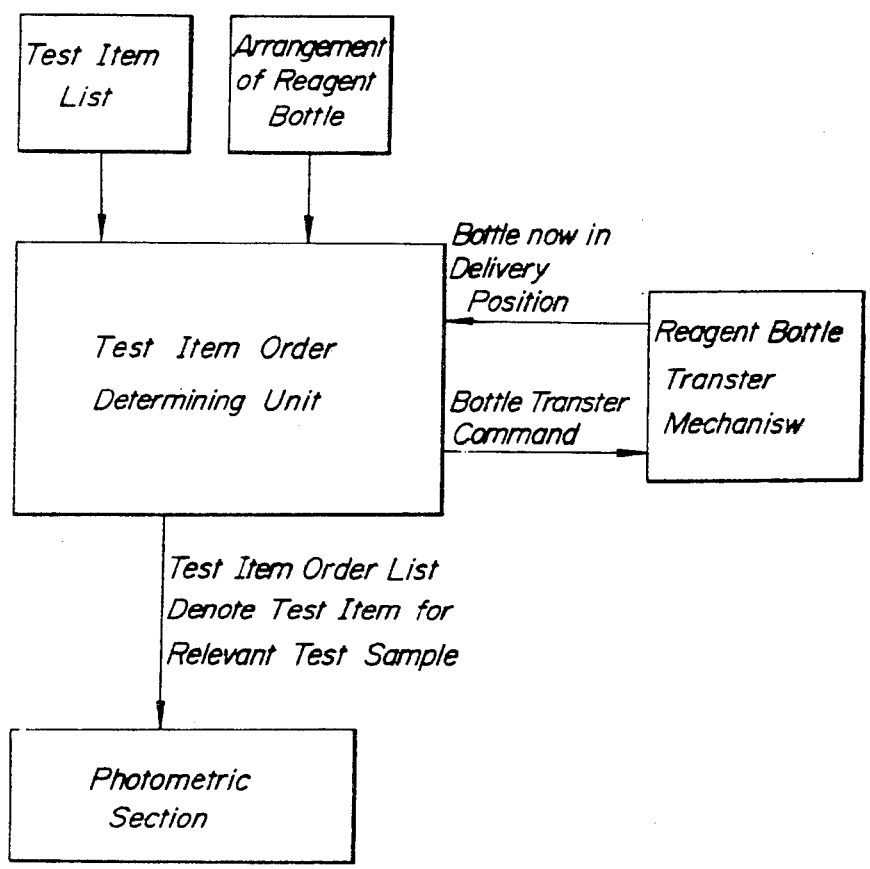
FIG. 15 is a block diagram showing a manner of controlling a reagent feed mechanism for minimizing a total travelling distance of the reagent cassette.

As illustrated in FIG. 15, information about the order of arrangement of reagent bottles in the cassette has been previously stored in a test item order determining unit. Upon an initiation of measurement for a particular test item, test item data to be effected for the relevant test item is supplied from a memory to the test item order determining unit, to which is also supplied information about a particular reagent bottle which is now in the reagent aspiration position in the reagent bottle transfer device. In the determining unit, the test item order is determined on the basis of these three pieces of information in such a manner that the traveling distance of cassette in the holder can be minimized, and a list for denoting the determined test item order is formed. In accordance with this list the order determining unit controls the successive alignment of reagent bottles with the reagent aspiration station in a sequence so as to insure the optimum economy of movement on the part of the cassette. At the time the list is generated, the list is also supplied to the photometric section, so as to provide the photometric section with test item data relevant to the photometer's responsibilities, for example, the overall sequence of test items and samples on the turntable.

Figure 16:
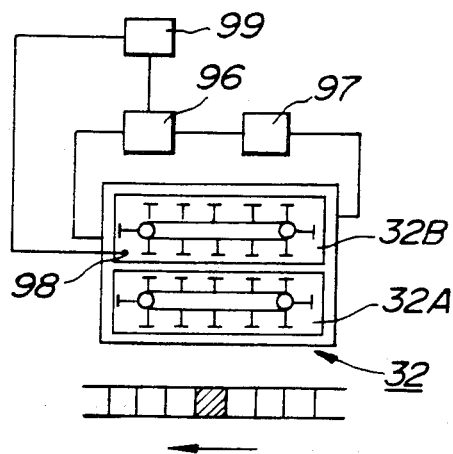
FIG. 16 is a schematic view illustrating an embodiment of the cassette holder comprising separate refrigerator and room temperature portion.
Figure 17:
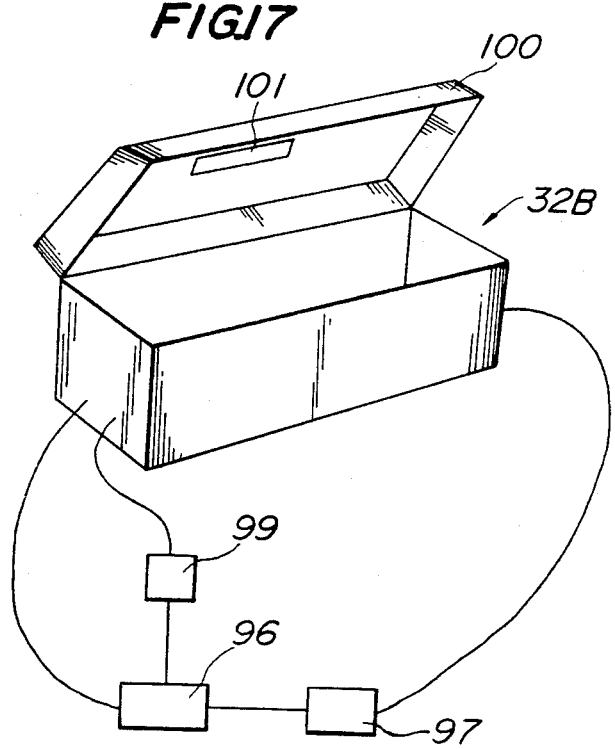
FIG. 17 is a perspective view showing an embodiment of the refrigerator of FIG. 16.

In the above embodiment, all the reagent bottles are arranged in a refrigerator in order to avoid an alternation of deterioration of the reagents. However, some reagents might precipitate under a low temperature and thus should not be stored in the refrigerator. In such a case, as shown in FIG. 16, the cassette holder 32 is divided into two portions, 32A and 32B. One portion (32A) is maintained at room temperature, and reagents which should not be stored at low temperatures are installed in this portion 32A. The other portion (32B) is connected to a refrigeration machine 96 and blower 97, to form a closed loop. The operation of the refrigeration machine 96 is controlled by a temperature-detecting element 98 in holder 32B, and a control circuit 99 which receives the output signal from temperature detector 98. It should be noted that the cassette shown in FIGS. 13 and 14 may be installed in portions 32A and 32B. In order to prevent the escape of cool air from refrigerator portion 32B, portion 32B comprises a lid 100 (illustrated in FIG. 17). A small aperture 101 is formed in the lid at a position corresponding to the aspiration position so that a fluid dispensing probe can be inserted into and retracted from portion 32B. The fluid which is used to calibrate the apparatus is preferably stored in refrigerator portion 32B.

Figure 18:
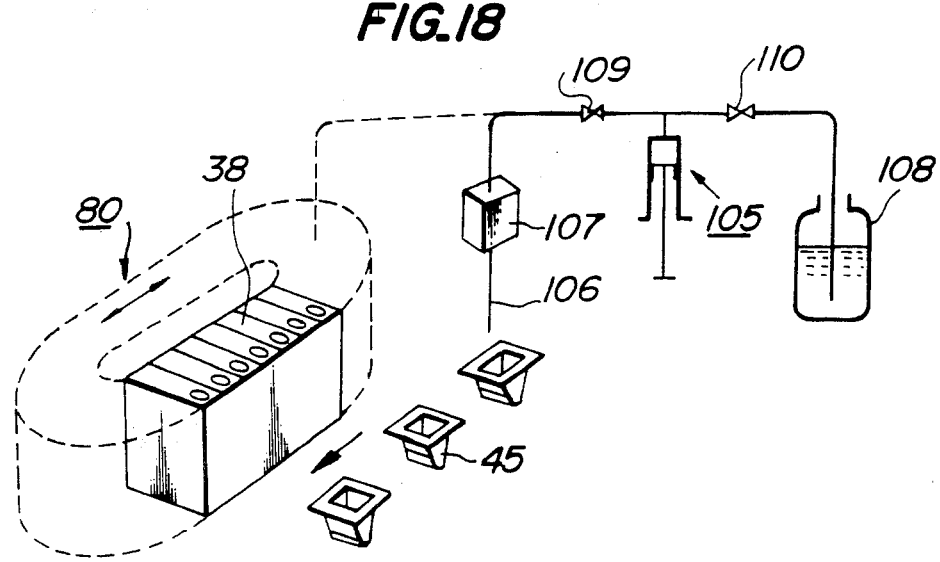
FIG. 18 is a schematic view explaining a delivery operation of the reagent delivery mechanism shown in FIG. 5.

In the reagent delivery mechanism as shown in FIG. 18, only a single pump 105 is able to deliver a plurality of different reagents.

In this embodiment, use is made of reagents of high concentration and the reagents are jetted into the cuvettes from the probes together with appropriate diluent(s). By utilizing this construction, the whole apparatus can be made small in size, and contamination between the different reagents can be avoided because the inside of probe is washed by the diluent(s). Since diluent(s) is/are heated to a temperature near the reaction temperature, the temperature of the test liquid can be rapidly increased, and the reaction time can be shortened even if the refrigerated reagent is used and the reaction is carried out in a temperature-controlled incubation environment having a low thermal efficiency, such as an air bath. Further, if the diluent is the same liquid as any required buffer solutions, it is not necessary to provide separate delivery pumps for these liquids.

To begin a dispensing cycle, the desired reagent bottle 38 in the cassette 80 is transported to a position just below the aspiration position of the probe 106. A preheating device 107 is provided to heat the diluent to a temperature near the desired reaction temperature and comprises a heater, a temperature sensor and a temperature control circuit (not shown). The syringe 105 is connected to the probe 106 and a diluent bottle 108 via valves 109 and 110, respectively. In this embodiment, these valves are denoted as two-way valves, but they may be replaced by a single three-way valve. Since these valves 109 and 110 are kept in contact with the diluent only, they do not require chemical resistance. However, in view of a very small amount of liquid to be delivered it is desired that a volume inside the path be kept within very narrow and precise limits. To this end, it is preferable to construct the valves 109 and 110 by use of a rotary solenoid valve with a tapered cock.

The syringe and piston constructing the pump 105 do not require special chemical resistance properties because like the valves 109 and 110 they contact only diluent liquid. In order to deliver different amounts of reagents by the same pump 105 the piston of the pump can be displaced by strokes of variable length by a pulse motor energized by an external signal. As the diluent use may be made of buffer solution as explained above or in some cases use may be made of de-ionized or distilled water.

Operational steps of the reagent delivery pump will be denoted in the following table.

| Step | Position of probe 106 | Valve 109 position | Valve 110 position | Syringe 105 piston motion |
|---|---|---|---|---|
| Form air bubble at probe tip | Stand by position (in air) | Open | Closed | Withdraw slightly |
| Probe into reagent | Stand by position → in reagent | Closed | Closed | None |
| Aspirate reagent | In reagent | Open | Closed | Withdraw to aspirate reagent |
| Transport probe above cuvette | In reagent → above cuvette | Closed | Closed | None |
| Deliver reagent and diluent into cuvette | Above cuvette | Open | Closed | Close to dispense |
| Aspirate diluent | Above cuvette → stand-by position | Closed | Open | Withdraw to aspirate diluent |

Figure 19:
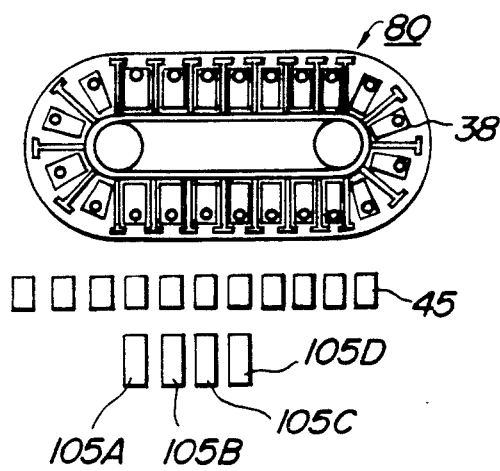
FIG. 19 is a schematic view showing an embodiment of the reagent delivery mechanism.

When different diluents are used for different reagents, or when a reagent is delivered at several positions, a plurality of delivery pumps 105A to 105D may be provided for each diluent as shown in FIG. 19. When a cuvette 45 is transported to a delivery position corresponding to any one of the pumps 105A to 105D, for example 105A, and the reagent to be delivered to this cuvette is that which should be diluted by a diluent connected to this pump 105A, the related reagent bottle 38 is fed to a position corresponding to the pump 105A and then a given amount of the desired reagent is delivered into the cuvette 45 by the pump 105A. On the contrary, if the reagent to be delivered to this cuvette is that which should be diluted by a diluent connected to the pump 105C, after the cuvette is further advanced by two steps, the desired reagent is delivered into the cuvette 45 by the pump 105C.

According to the above explained construction of the reagent delivery mechanism, since the diluents or buffer solutions which are optimum for respective diluents can be used, the reagents can be maintained in a stable condition for a longer time, and the number of possible test items can be increased. For some reagents it is preferable to effect delivery thereof by several stages in order to effect storage of the reagents as component parts in such a way as to prolong the useful chemical stability of these reagents or to dispense quantities which may be beyond the useful dynamic range of a given pump 105A to 105D. In such a case, the same reagent or its component part may be delivered into the same cuvette by a succession of pumps 105A to 105D at successive steps.

In such a discrete delivering operation it is quite important to assure whether a given amount of liquid has been aspirated or not. That is to say, if a serum, sample, or reagent is aspirated excessively or insufficiently, erroneous data would be obtained. Therefore, such a situation must be checked by some means.

FIG. 20A is a schematic perspective view illustrating an embodiment of such means for detecting an amount of aspirated liquid. In this embodiment, the probe 106 is made of transparent material and a light emitting element 110 and a light receiving element 111 are arranged on respective sides of the probe 106. In the probe 106 there are liquid 112 such as a reagent or sample, an air layer 113 and a diluent 114, these materials having different absorptions. Therefore, a transmittivity T represented by an output from the light receiving element 111 changes as shown in FIG. 20B, depending upon a volume Q of the aspirated liquid 112. From this output T it is possible to detect whether or not a correct amount of liquid has been drawn in the probe.

In an embodiment shown in FIG. 21A, a pair of electrodes 115 and 116 are arranged in the probe 106 with interposing a given distance therebetween. When a correct amount of the liquid 112 has been aspirated in the probe, these electrodes 115 and 116 are conductively connected to each other via the electrically conductive liquid so as to identify the correct amount of liquid. FIG. 21B illustrates a characteristic curve denoting a relation between the amount of aspirated liquid Q, and a resistance value R, between the electrodes.

In another embodiment illustrated in FIG. 22A, a pair of plate-shaped electrodes 117A and 117B are arranged on either side of the probe 106 so as to form a capacitor. The capacitance between plates 117A and 117B will be a function of the liquid level in the probe 106. The capacitor is connected to a CR oscillator 119 which will change frequency as capacitance changes. Liquid level in probe 106 will now be determined by frequency of CR oscillator. The output frequency of the oscillator f varies as a function of an amount Q of the liquid 112 (see FIG. 22B). The output signal is counted by a counter 120 and an output from the counter is supplied to a discrimination circuit 120 to determine whether the amount Q of the aspirated liquid 112 is correct or not.

Figure 23:
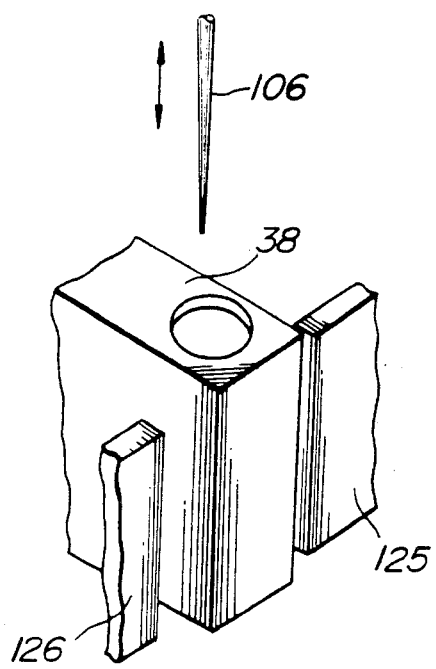
FIG. 23 is a perspective view illustrating an embodiment of a liquid level detector for a reagent in a reagent bottle.

When the reagent is aspirated by the reagent delivery probe which is immersed in the reagent as explained above, it is preferable to detect the level of the reagent in the bottle so as to control the depth of that portion of the probe which is immersed in the reagent. FIG. 23 is a perspective view showing schematically an embodiment of such a liquid level detector. In this embodiment, the reagent bottle 38 is made of transparent material and a light-emitting device 125 and a light-receiving device 126 are arranged on respective sides of the bottle 38. These devices comprise a plurality of light-emitting and receiving elements, respectively, arranged side by side in the vertical direction, and the liquid in the bottle 38 can be detected by output signals from these light-receiving elements. With the aid of these signals the immersed depth of the probe 106 of the reagent delivery pump 105 can be controlled in a desired manner.

By the above explained measure, it is possible to draw positively a given amount of reagent with inserting the probe 106 into the reagent by the minimum required depth and thus, an amount of reagent adhering to the outer wall of probe can be minimized. Therefore, the tip of probe can be easily and positively washed, and any contamination between the reagents can be effectively eliminated.

Figure 24:
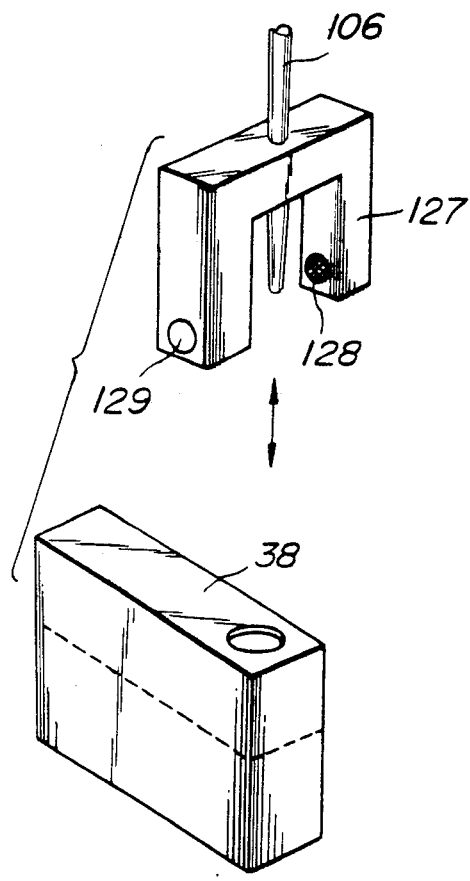
FIG. 24 is a perspective view showing another embodiment of the reagent level detector.

The liquid level detector may be constructed as illustrated in FIG. 24. In this embodiment, a holder 127 is secured to the probe 106 and a light-emitting element 128 and a light-receiving element 129 are provided at respective ends of arms of the holder 127. The reagent bottle 38 is made of transparent material. By lowering the holder 127 together with the probe 106 the liquid level of the reagent in the bottle 38 can be photoelectrically detected.

Figure 25:
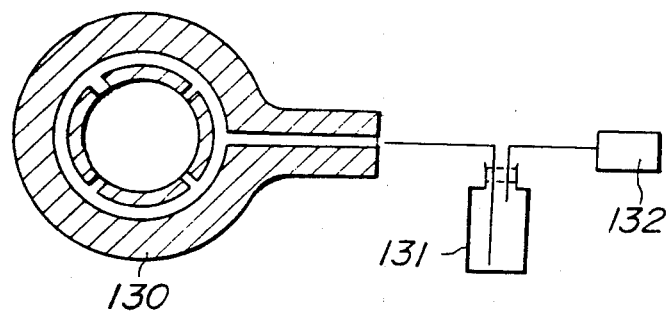
FIG. 25 is a schematic view showing an embodiment of a probe washing device.

Next, a device for cleaning the probe of the reagent delivery pump will be explained. FIG. 25 is a schematic cross section illustrating an embodiment of such a cleaning device. In this embodiment, a ring 130 having a plurality of openings in its inner wall is connected through a waste liquid bottle 131 to a vacuum pump 132. The probe is inserted into the ring 130 and the pump 132 is energized to aspirate a liquid adhering to the outer surface of the probe into the bottle 131.

Figure 26:
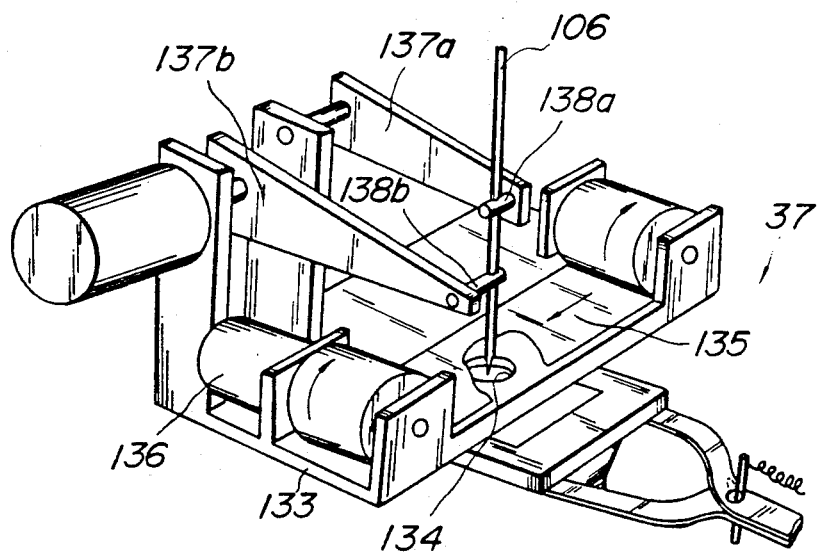
FIG. 26 is a perspective view depicting another embodiment of the washing device.

FIG. 26 is a perspective view illustrating another embodiment of the cleaning device. In this embodiment, by piercing the probe through a blotter, a reagent on the outer surface of the probe can be removed. To this end, a supporting plate 133 is arranged above the reaction line of cuvette feed mechanism 37 in parallel with the reaction line. The supporting plate 133 has formed therein an opening 134 for passing the probe, and a blotter 135 is passed through the opening. The blotter 135 is wound onto a roll which is rotatably supported at one end of the plate 133. At the other end of the plate a motor 136 is provided which takes up the blotter 135. It should be noted that a suitable load may be applied to the blotter roll so as to avoid looseness of the blotter. Upon delivering the reagent, the probe 106 is inserted into the cuvette 45 on the reaction line through the blotter 135 and the aperture 134.

Figure 27A:
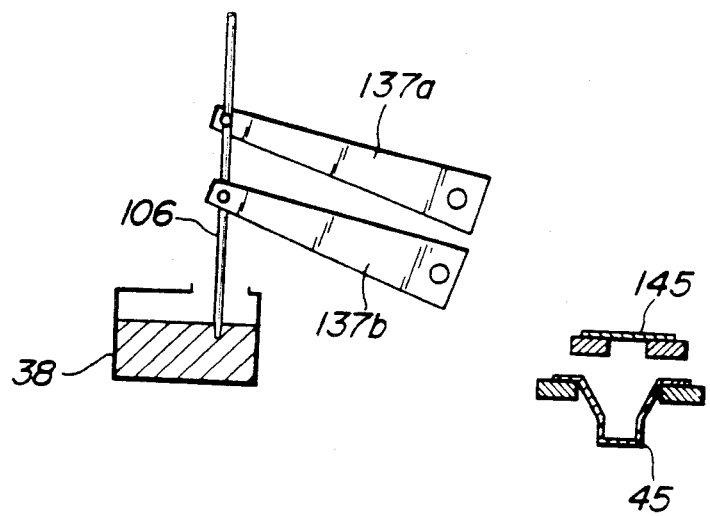
FIGS. 27A and 27B are schematic views for explaining the operation of the washing device shown in FIG. 26.
Figure 27B:
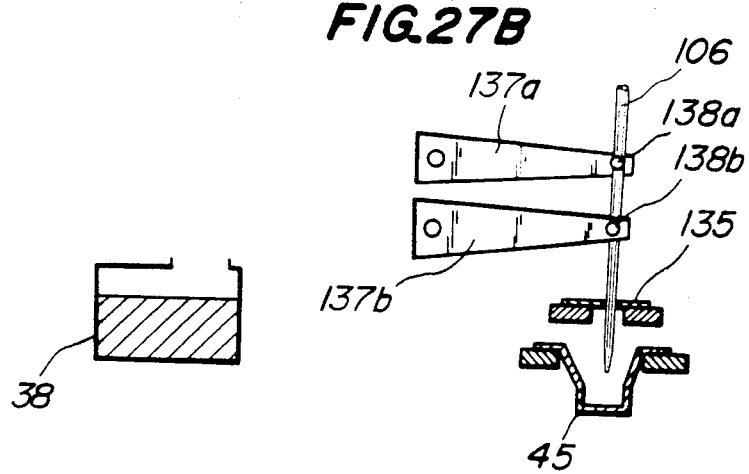

In this embodiment, a pair of arms 137a and 137b are rotatably journaled to the supporting plate 133 and the probe 106 is rotatably supported at the free ends of arms by means of pins 138a and 138b. To one of the arms 137b is coupled a motor 139. The probe 106 can move between the arms 137a and 137b into the reagent bottle 38 at the reagent aspirating position as shown in FIG. 27A, as well as into a position above the cuvette 45 through the blotter 135 and the opening 134, as illustrated in FIG. 27B. In this case, it is preferable to use the liquid level detector shown in FIG. 23.

In the above explained probe-washing device, since it is not necessary to use a wash water, the construction becomes simple, and the probe 106 can be completely cleaned in conjunction with the liquid level detector.

The above explained probe-washing device and its transporting mechanism may be also applied to the probe of the sample delivery mechanism 36.

Next, a control device for controlling the actions of each portion of the analyzing apparatus, introducing test body information, treating and displaying analyzed results and the like will be explained. As stated above, in the present embodiment, the control device is arranged apart from the analyzing apparatus itself. When the analyzing apparatus is separated from the control device, (1) when the analyzing apparatus is installed in a laboratory hospital or the like which has a computer of sufficient capacity, the analyzing apparatus can be controlled by supplying appropriate software to this computer, (2) in case a dedicated control device becomes out of order, by selectively connecting the analyzing apparatus with a transmission circuit, the analyzing apparatus can be operated by a back-up computer connected through the transmission circuit, and (3) in case an increase in productivity is necessary, a single control device can operate a plurality of analyzing apparatuses by adding one or more analyzing apparatuses to the analyzing apparatus already in operation.

Figure 28:
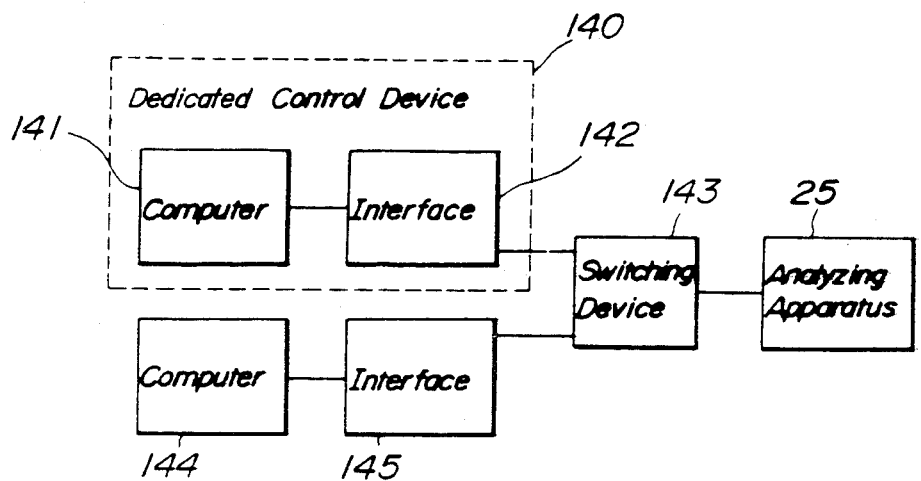
FIG. 28 is a block diagram showing a manner of connecting the automatic analyzing apparatus according to the invention to a computer installed at a hospital.

The constructions for carrying out the above functions (1) to (3) will be explained in order. FIG. 28 is a block diagram showing the construction of an automatic analyzing apparatus according to the present invention, in which control of the automatic analyzing apparatus is switchable between a dedicated control device and some other computer system such as a lab's host computer system. A dedicated control device 140 comprises a computer 141 and an interface 142 and is connected to an analyzing apparatus 25 through a switching device 143. Further, an alternate computer 144 can be connected to the analyzing device 25 through an interface 145 and said switching device 143. In this manner, the switching device 143 is automatically or manually operated, and the analyzing apparatus 25 is connected to either the dedicated control device 140 or the alternate computer 144.

According to such construction, if the dedicated control device 140 is down, the alternate computer 144 can serve as back-up by operating the switching device 143, so that there is no interruption in analyzing operation. Further, the computer 144 can be operated without affecting the dedicated control device 140.

Figure 29:
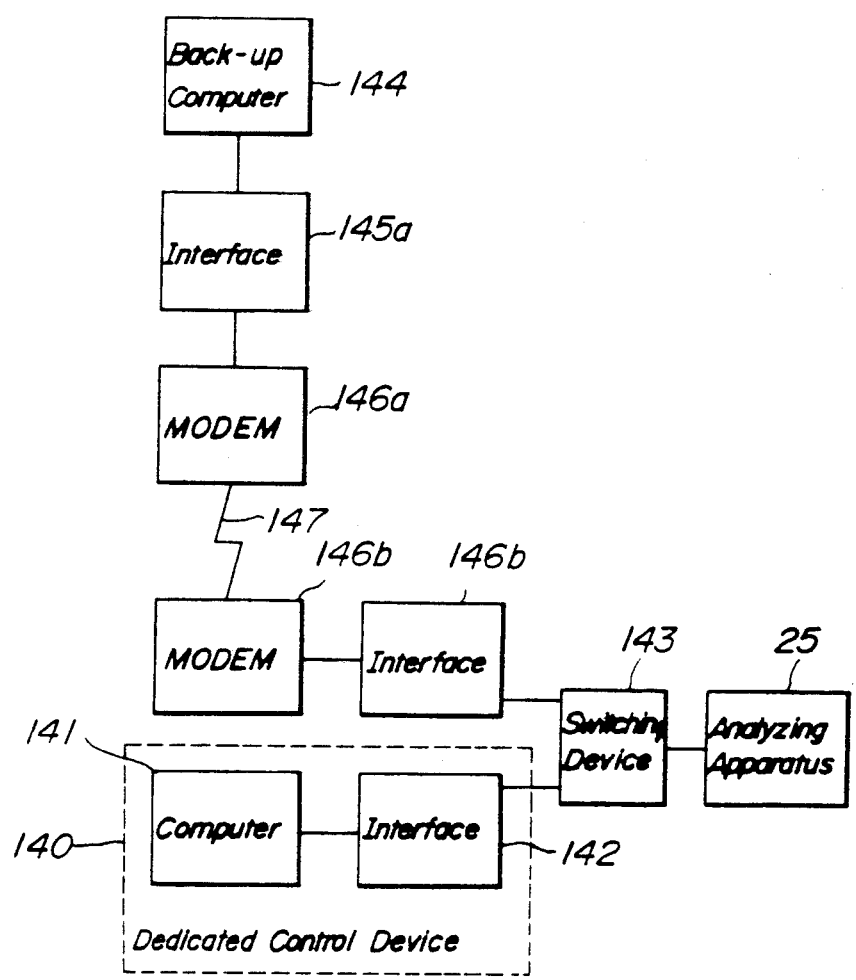
FIG. 29 is a block diagram illustrating a manner of coupling the apparatus according to the invention with a back-up computer through a communication line.

FIG. 29 is a block diagram showing another embodiment of the system, including the automatic analyzing apparatus according to the present invention, in which the automatic analyzing apparatus is connectable with a back-up computer through a communication line. Like numerals indicate like parts as shown in FIG. 28. A back-up computer 144 is connected to a communication line 147 through an interface 145a and a MODEM 146a. This back-up computer 144, interface 145a and MODEM 146a are installed in a service company, maker, or the like. On the side of the provisions provided with the analyzing apparatus 25, is provided a MODEM 146b connected to said communication line 147 and further connected to the switching device 143 through an interface 145b. In this manner, the switching device 143 can be automatically or manually operated, and the analyzing apparatus 25 is then connected to either the back-up computer 144 or the dedicated control device 140.

According to such construction, as described above, even if the dedicated control device 140 becomes out of order, the back-up computer 144 can operate the analyzing apparatus 25 through the communication line 147 until repair is completed so that there is prolonged interruption in analyzing operations.

Figure 30:
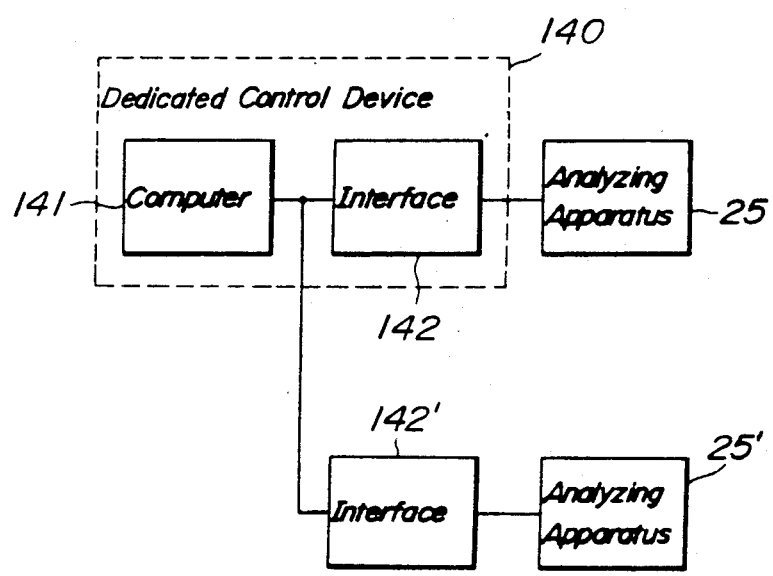
FIG. 30 is a block diagram showing a manner of controlling or operating a plurality of the analyzing apparatuses according to the invention by means of a single controlling unit.

FIG. 30 is a block diagram showing still another embodiment of the system comprising the automatic analyzing apparatus according to the present invention, in which one control device can operate a plurality of analyzing apparatuses. In this embodiment, like numerals indicate like parts as shown in FIG. 28. In this embodiment, a computer 141 in one dedicated control device 140 can be connected to one analyzing apparatus 25 through an interface 142 as well as to an additional analyzing apparatus 25' through an interface 142'.

According to such construction, a plurality of the analyzing apparatuses 25, 25' can be controlled by the single control device 140 so that productivity can be increased expeditiously and economically.

A patient data system for use with an automatic analyzing apparatus according to the present invention will be explained.

In a conventional automatic analyzing apparatus, a commonly used patient data system begins with a test requisition form which, in a clinical setting, is usally filled out by, or under the direction of, a given patient's attending physician. This filled-in requisition form includes the patient's name and/or an identifying number and the tests for which the sample must be analyzed as minimum information.

The various test requisition forms are used to prepare a loading list. The loading list describes each sample's identification (by name and/or number) and its position on the instrument's sampler and/or its place in the sample queing. Test results are generated in the same sequence as samples are introduced, and the relationship between test results and the corresponding patient can be determined from the loading list. The analytical results can be manually transferred to the requisition slip for use as the report form ultimately returned to the attending physician or; the patient identification information can be manually transferred to the standard instrument report form or; both the analytical results and the patient information can be manually transferred to yet another form to serve as the physician's report.

In such a patient data system, however, it is necessary to copy the analytical results and/or patient information. Further, in case of deleting or adding a sample, or inserting a stat (urgent) sample by squeezing it between samples, the relation between the analyzed results and the loading list changes and the following mistakes can occur.

1. Mistaken match of sample number to patient name.
2. Posting mistake of patient information and/or analytical results.
3. Mistaken match of sample aliquot to identification name and/or number.
4. Proper match of sample and identification number, but mistaken match to patient name.

Another common patient data system involves transferring patient data from the requisition form into a computer memory and printing it out together with analytical results. In this system, however, the patient information must be transferred manually by means of a keyboard, so that it is subject to a loading mistake. In yet another system, test item selection information is automatically loaded into a computer memory from a requisition card, but sample I.D. is manually collated with a patient, so that there is the possibility of a mistake similar to those described above.

Conventional automatic analyzing systems frequently include as part of the instrument report form some means for flagging or highlighting abnormal test results. Usually an expected range of values are predetermined and any test result outside this range of values is somehow flagged as 'a abnormal' on the instrument report form. However, patient populations differing by such things as age, sex, or the like, will have different expected ranges. For improved diagnostic information, it would be more appropriate to compare a given patient's results against those of an appropriate population.

The patient data system for the automatic analyzing apparatus according to the present invention eliminates various inconveniences in the above described conventional data systems while improving upon the integrity of data by reducing opportunities for error to occur.

The data system of the present invention utilizes a copy of the physician's original requisition form to obtain pertinent patient data and test selection information. The same form is used to provide an inseparable link between patient name and sample number and to serve as the instrument report form which includes patient identification data, sample number, analytical results, population appropriate expected ranges, and abnormals flagging (when appropriate). As a result of this data system, the possibility for the above mentioned errors has been eliminated. In addition, this system reduces the amount of paper which must be handled and consumed since the present invention uses the original test requisition form as the report form.

Figure 31:
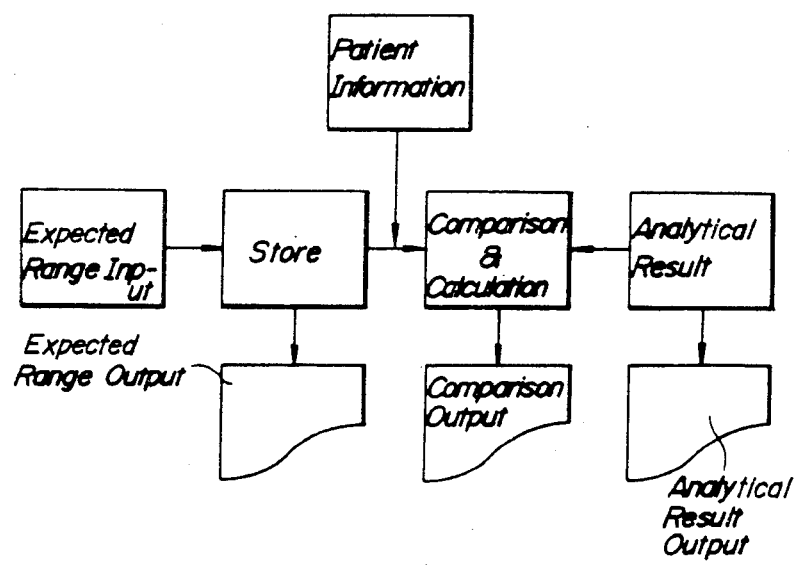
FIG. 31 is a flow chart showing an embodiment of a patient data system using the apparatus according to the invention.
Figure 32:
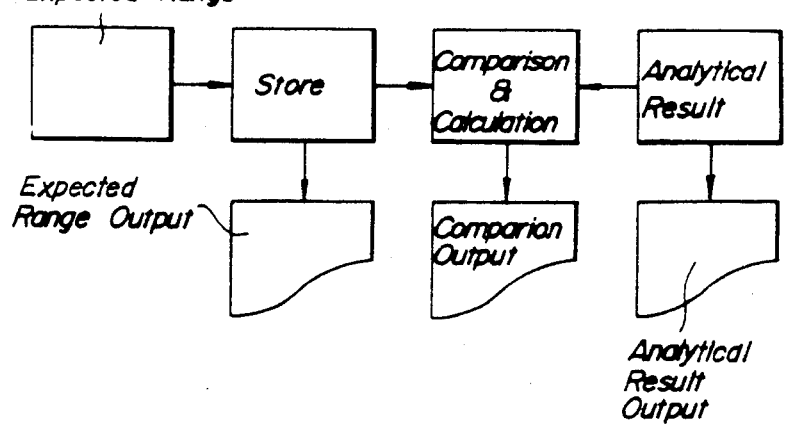
FIG. 32 is a flow chart showing another embodiment of the patient data system.

FIGS. 31 and 32 are flow charts of a patient data system of the automatic analyzing apparatus according to the present invention. FIG. 33 is a plan view showing a format of a patient card used in such system. The flow chart shown in FIG. 31 indicates that the various expected ranges by test item and population parameters (sex, age, medical prescription, and the like), have been previously stored in the analyzing apparatus and expected values corresponding to the patient's appropriate parameters are printed on the requisition/report form. On the requisition/report form, the analytical results and judgements obtained by comparing the analytical results against appropriate expected range values are also printed out. In the flow chart of FIG. 32, the patient information and the expected range values corresponding to the relevant patient have been previously recorded on the requisition/report form and the analytical results and judgements are subsequently printed on the form. In this case, the requisition/report form is fed through the reader/printer twice. During the first feed, the test item selection information and the patient's expected range population parameters corresponding to an identifying number are read out and appropriate expected ranges are printed on the form. As shown in FIG. 33, use is made of a bar code for the identifying number. When abnormal analytical values are detected, judgements are printed in an AF (Abnormal Flags) column with marks for indicating the direction of deviation from the expected range and an amount of abnormality (for example: the number of standard deviations the analytical result differs from the mean expected value.)

Next, a mechanism for disposing a cuvettes and test liquids after photmetric measurement will be explained. In this embodiment, waste liquids are not discharged from the analyzing apparatus. In the apparatus is provided a waste liquid handling mechanism for pretreating chemical wastes before allowing their removal from the system so as to facilitate their disposal via environmentally responsible means.

Figure 34:
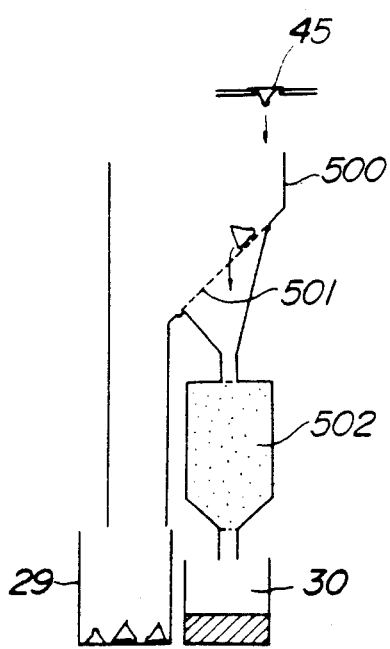
FIG. 34 is a schematic view showing an embodiment of a cuvette and liquid discharging mechanism.

FIG. 34 is a schematic diagram showing an embodiment of such a disposal mechanism. The cuvette 45 is held by the supporting mechanism at each photometric position of the photometric measurement section. After measurement, the supporting mechanism is driven and the cuvette 45 is allowed to fall (as shown in FIG. 34 by an arrow). Underneath the cuvette 45 is arranged a duct 500 on which a mesh 501 is in an inclined fashion. The falling cuvette 45 strikes the mesh 501 and the content of cuvette is spilled into a neutralizing tank 502. The cuvette 45 slides downward on the mesh 501 until it is allowed to fall into the cuvette waste tank 29. In the neutralizing tank 502, the pH value of the waste liquids is adjusted and noxious substances are remove. The filtration is then passed to the waste liquid container 30. The neutralizing tank 502 is arranged in such a way as to be conveniently removable and if its treating ability is diminished, it may be regenerated or exchanged.

According to such a disposal mechanism, even if the waste liquid is temporarily stored in the container 30, annoying odors due to noxious substances would not be produced. Additionally, solid and liquid wastes are conveniently separated for disposal.

Figure 35:
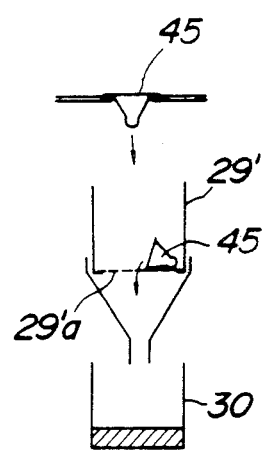
FIG. 35 is a schematic view showing another embodiment of the discharging device.
Figure 36:
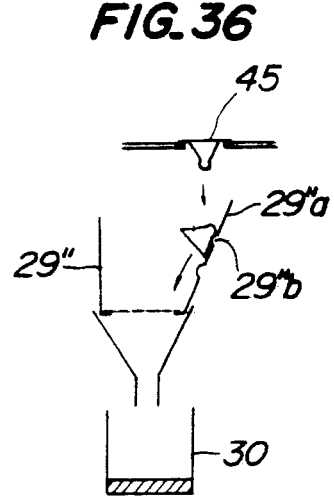
FIG. 36 is a schematic view showing still another embodiment of the discharging device.

FIGS. 35 and 36 are schematic views illustrating two other embodiments of disposal mechanism. In FIG. 35, the cuvette 45 falling from the cuvette-supporting mechanism is received by a cuvette container 29' having secured a mesh 29a' at its bottom, and the waste liquid is supplied into the container 30. Since the cuvette 45 has a shape shown in FIG. 11, it rolls easily. Therefore, the liquid in the cuvette can be completely discharged. FIG. 36 shows the construction similar to that shown in FIG. 35, except that the falling cuvette 45 is positively turned on the inner wall of a cuvette container 29". To this end, an inclined side wall 29a" of the container 29" is provided beneath the path of a falling cuvette and discontinuous projections 29b" are formed in the inner surface thereof.

According to such constructions similar to that in FIG. 34, solid and liquid wastes can be automatically separated to facilitate waste treatment and disposal.

Figure 37:
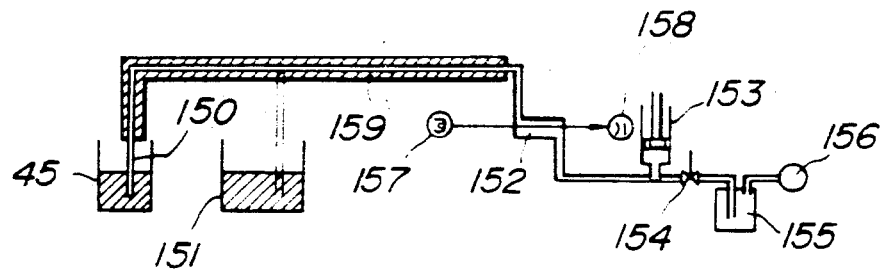
FIG. 37 is a schematic view showing another embodiment of the apparatus according to the invention.

It should be noted that the present invention is not limited to the embodiments mentioned above, but many modifications can be conceived within the scope of the invention. For instance, in the above embodiment, the lag phase is monitored before the photometric measurement in the linear phase is effected, but the end point may be monitored by the lag phase monitoring section and after the end point has been detected, the photometric measurement may be carried out. In the embodiment, after the detection of the end of the lag phase by the monitoring section, the test liquid is removed from the reaction line together with the cuvette and the precise measurement is effected. However, as shown in FIG. 37, it is possible to transport the test liquid alone from the reaction line to the precise measuring section. In FIG. 37, a suction nozzle 150 is arranged movably from the cuvette 45 on the reaction line to a washing bottle 151. The nozzle 150 is connected to a syringe 153 through a heat-insulated tube 159 and a flow-type photometric cuvette 152. The syringe 153 is coupled to a suction pump 156 via a valve 154 and a waste liquid tank 155. A precise measuring photometer comprises a light source 157 and a photometric converter 158 arranged on respective sides of the photoelectric cuvette 152. The valve 154 is closed and the nozzle 150 is immersed into the test liquid in the cuvette 45 on the reaction line after the content of the cuvette has been detected to be in the linear phase, and the syringe 153 is operated to draw a given amount of the test liquid. Then, the nozzle 150 is moved into the washing bottle 151 and the syringe 153 is operated again to aspirate a washing water so that the previously aspirated test liquid is fed into the photometric cuvette 152. Then, the aspirating operation of washing water is stopped and the precise measurement is effected by means of the photometer 157 and 158, while the test liquid is in the cuvette 152 stationarily. After measurement, the valve 154 is opened and the pump 156 is energized to discharge the test liquid and washing water aspirated in the cuvette 152 and the tube 159 into the tank 155. During this operation, the syringe 153 is returned in its initial position. Since the suction nozzle 150 and the photometric cuvette 152 are washed with water after measurement, any contamination does not occur. The suction and measurement may be carried out in the manner mentioned below. At first, the valve 154 is closed and the syringe 153 is operated to draw the test liquid into the cuvette 152. Then, the precise measurement is effected. After the measurement, the valve 154 is opened and the pump 156 is driven to suck the washing water. At the same time, the syringe 153 is returned to the initial state. Also in this case, the precise photometric measurement can be effected without any contamination.

Figure 38:
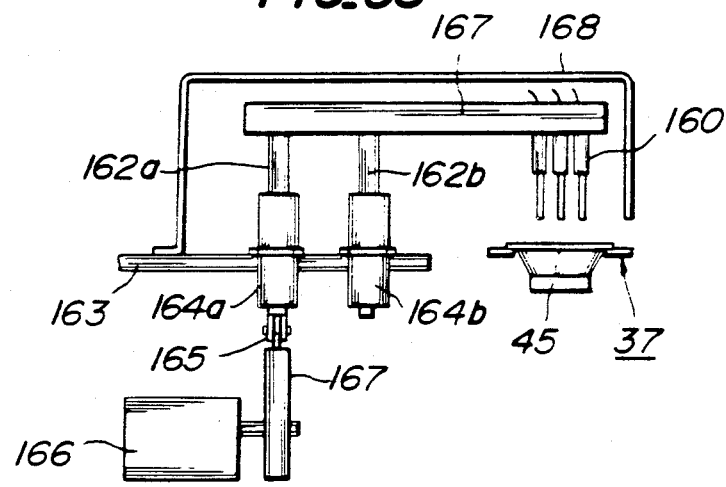
FIG. 38 is a schematic view showing an embodiment of an ion concentration measuring device which may be installed in the apparatus according to the invention.

To improve upon analytical capabilities of the present invention it is further possible to provide an ion activity measuring device at any position on the reaction line after the reagent delivery so as to measure concentrations of ions of such potential test items as Na, K, Cl, etc. FIG. 38 illustrates an embodiment of such a device.

In this embodiment, a plurality of ion selective electrodes 160 are immersed in the cuvette 45 set in the cuvette feed mechanism 37 (reaction line) to measure the ion concentration. These electrodes 160 are secured to one end of an arm 161, to the other end of which is secured a pair of guide rods 162a and 162b, which are inserted to as to allow movement in sleeves 164a and 164b, respectively, provided in a supporting plate 163. At the free end of the guide rod 162a is journaled a roller 165, which is urged against an eccentric cam 167 which is secured to a driving shaft of a motor 166. In order to avoid dust contamination, the ion activity measuring device is protected by a cover 168. As the cam 167 is rotated by the motor 166, the arm 161 moves up and down vertically, while it remains horizontal owing to the sleeves 164a and 164b. When the arm 167 is lowered, the ion selective electrodes 160 are immersed in the test liquid in the cuvette 45 to measure simultaneously various ion activities.

Figure 39:
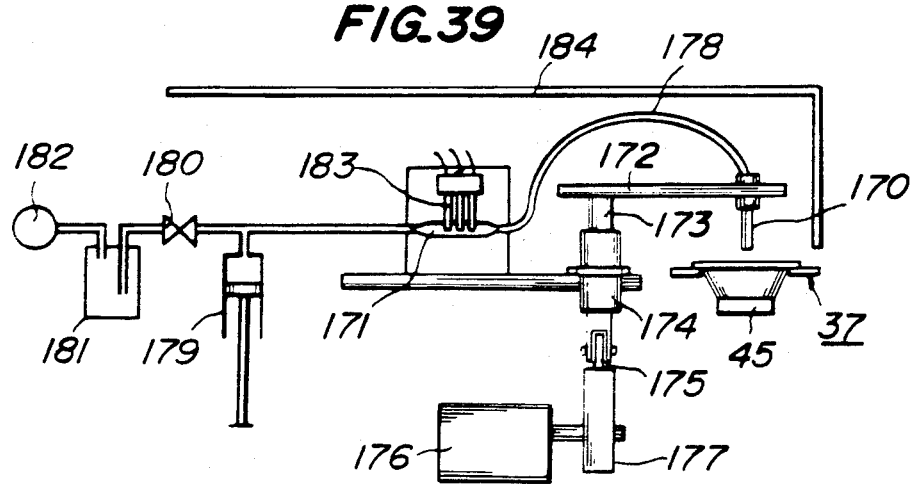
FIG. 39 is a schematic view showing another embodiment of the ion concentration measuring device.

FIG. 39 is a schematic view illustrating another embodiment of the ion activity measuring apparatus. In this embodiment, the test liquid in the cuvette 45 is aspirated by a nozzle 170 into a flow cell 171 in which various kinds of ions can be detected. The nozzle 170 is secured to one end of an arm 172, the other end of which is secured to a guide rod 173. The guide rod 173 is inserted so as to allow movement in a sleeve 174 which is secured to a supportng plate. A roller 175 is secured so as to allow rotation at one end of the guide rod 173, and is urged against an eccentric cam 177 which is secured to the driving shaft of a motor 176. When the cam 177 is rotated by the motor 176, the nozzle 170 is immersed into the test liquid in the cuvette 45. The nozzle 170 is connected to a syringe 179 through a flexible tube 178 and a flow cell 171 and to a suction pump 182 through a valve 180 and a waste liquid tank 171. The ion selective electrodes 183 are arranged in such a manner that their measuring surfaces project into the flow cell 171. In order to protect the apparatus against dust, a cover 184 is provided. At first, the valve 180 is closed and the nozzle 170 is immersed into the test liquid in the cuvette 45 on the reaction line by energizing the motor 176. Then, the syringe 179 is operated to aspirate a desired given amount of the test liquid in the cuvette 45 into the flow cell 171. Under such a condition, concentrations of various ions in the test liquid are quantitated by the ion selective electrodes 170. After measurement, the valve 180 is opened and the pump 182 is energized to discharge the test liquid into the tank 181 and the sryinge 179 is returned to its initial position.

Figure 40:
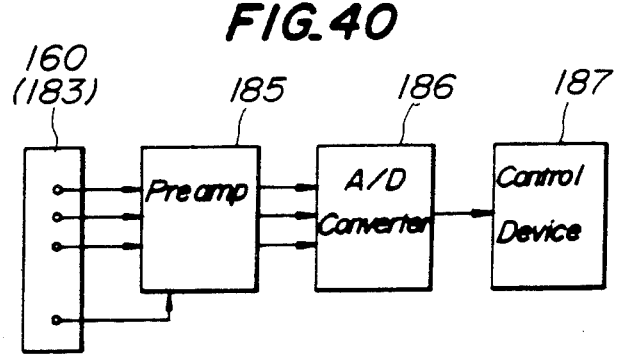
FIG. 40 is a block diagram showing an embodiment of a signal processing circuit of the ion concentration measuring devices shown in FIGS. 38 and 39.

FIG. 40 is a block diagram showing an embodiment of a signal processing circuit of the above mentioned ion activity measuring device. Output signals from the ion selective electrodes 160 (183) are amplified in a preamplifier 185 and then are converted into a digital signal by an analog-digital converter 186. The digital signal thus obtained is supplied to a control device 187 and is processed in a desired manner therein.

In the ion activity measuring device shown in FIGS. 38 and 39, a blotter may be arranged above the reaction line as illustrated in FIG. 26 and the ion selective electrodes 160 and the nozzle 170 may pierce the blotter. Alternatively, a wash bottle may be arranged apart from the reaction line as depicted in FIG. 37 and the ion selective electrodes and the nozzle can be immersed in this bottle. In this manner, the ion selective electrodes and the nozzle can be cleaned so as to avoid any contamination between successive test liquids and thus very accurate measurement can be conducted.

Figure 41:
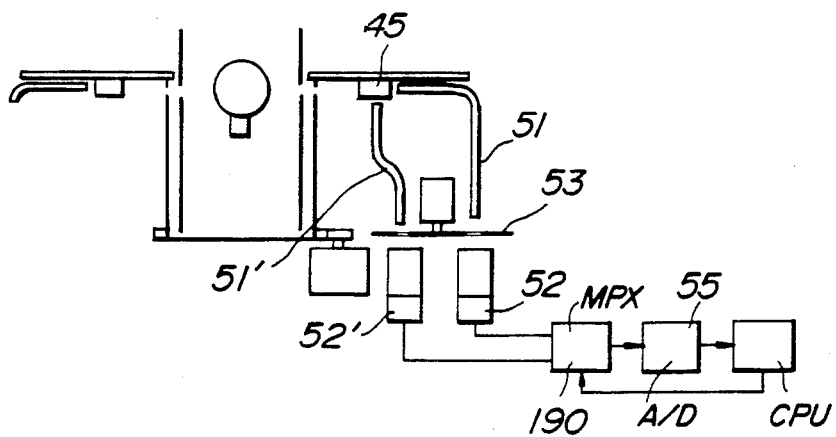
FIG. 41 is a cross section showing schematically an embodiment of a photometric section of the apparatus according to the invention, which can effect colorimetric, nephelometric and fluorometric analyses.

Further, in the above embodiments, the measuring section 42 is so constructed as to analyze test items in a test liquid by means of a standard photometric method, but use may be made of nephelometric and fluorometric methods in addition to the standard photometric method. In such a case, a light-receiving element 52' for receiving scattered and/or fluoroscent light, may be arranged underneath the cuvette 45 in the required measuring position as shown in FIG. 41. The light-receiving element, a photodetector device 52', may be arranged underneath the rotary filter unit 53 shown in FIGS. 7 and 41 and may be effectively opposed to the cuvette 45 by means of optical fibers 51.

Figure 42:
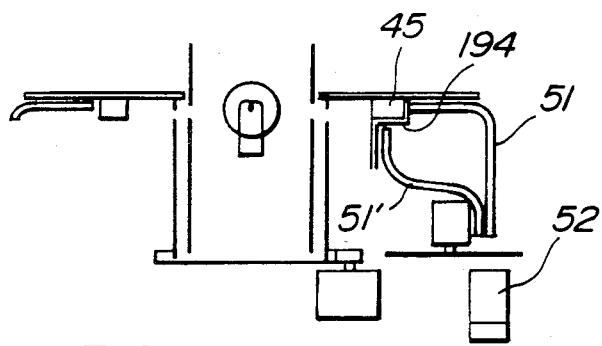
FIG. 42 is a cross section showing schematically another embodiment of the photometric section.
Figure 43:
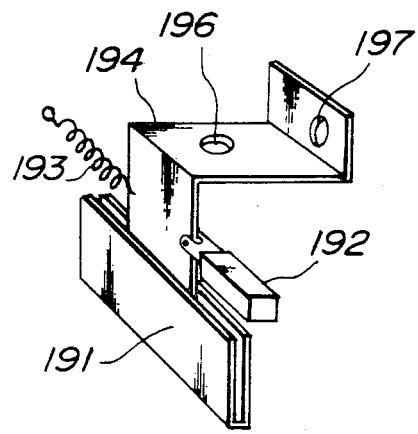
FIG. 43 is a perspective view showing an embodiment of a shutter mechanism shown in FIG. 42.

Outputs from these photodetectors 52 and 52' are supplied to an analog-digital converter 55 through a multiplexer 190. Further, as shown in FIG. 42, a common photodetector 52 for photometric measurement may be used also for nephelometric and/or fluorometric measurements with use of a shutter mechanism shown in FIG. 43 is made. This shutter mechanism comprises a guide plate 191 and a plate 194 which is moved along the guide plate against a force of a spring 193 by actuating a solenoid 192. The plate 194 has formed therein, an aperture 196 for standard photometric measurement, and an aperture 197 for passing the scattered and/or fluorescent light therethrough.

Figure 44:
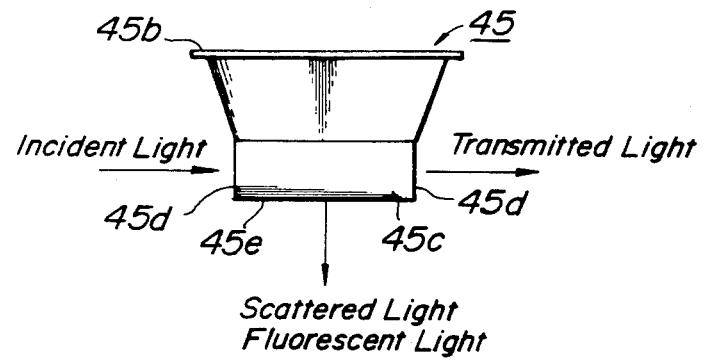
FIG. 44 is a side view illustrating an embodiment of the cuvette.

In case of effecting the nephelometric and/or fluorometric analyses by utilizing the scattering and/or fluorescent light from the test liquid, it is preferably to form the bottom portion 45c of the cuvette 45 as a flat surface 45e instead of a semicylindrical bottom surface as illustrated in FIG. 44. In this manner, it is possible to further increase the utility of the current invention by providing for additional measurement techniques, i.e. nephelometryc and/or fluorometry.

Figure 45:
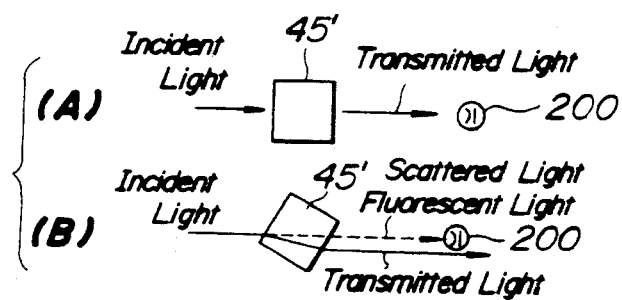
FIGS. 45A and 45B are schematic views illustrating an embodiment of the photometric section in which the transmitted, scattered and fluorescent lights are received by a single light receiving element.
Figure 46:
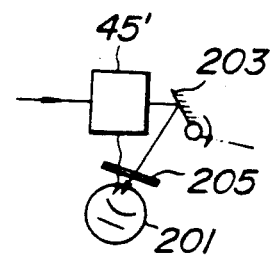
FIG. 46 shows another embodiment of the photometric section.
Figure 47:
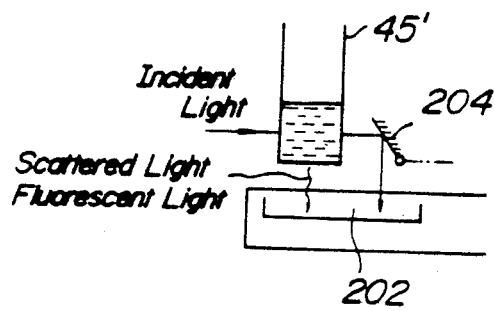
FIG. 47 illustrates still another embodiment of the photometric section.
Figure 48:
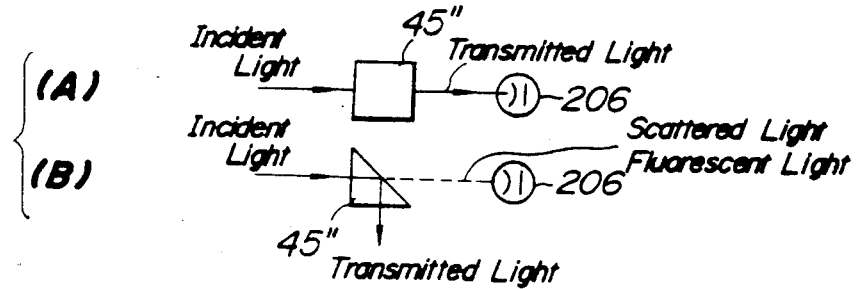
FIGS. 48A and 48B are schematic views illustrating another embodiment of the photometric section in which the scattered, transmitted and fluorescent lights can be received by a single element by using cuvettes having different configurations.

In the above embodiment for the nephelometric and fluorometric analyses, use is made of the light-receiving element separated from that of standard photometry, but a single light-receiving element may be commonly used for the transmitted, scattered and fluorescent light. FIGS. 45 to 48 show several embodiments of such capability. In FIG. 45, a cuvette 45' is so arranged that incident light impinges vertically upon a transparent incident surface and the light passing through the cuvette and the test liquid contained therein is received by an element 200 so as to effect the photometric measurement as shown in FIG. 45A. Then, the cuvette 45' is slightly rotated as shown in FIG. 45B, so that the transmitted light deviates from the optical axis of the element 200 and thus, the scattered light and/or the fluorescent light impinges upon the element 200. In this manner, the nephelometric and/or fluorometric analyses can be carried out. In FIGS. 46 and 47, the light-receiving elements 201 and 202 are so arranged that they can receive the scattered and/or fluorescent light, and transmitted light is directed to the element via a rotating mirrors 203 and 204. In FIG. 46, the scattered and/or fluorescent light from a side wall of the cuvette 45' impinges on the element 201 through a scattering element 205. In FIG. 47, the scattered and/or fluorescent light from the bottom of the cuvette 45' impinges on the element 202. When performing standard photometric analysis, the rotating mirrors 203 and 204 are positioned as shown in the drawings and the transmitted light is received by the elements 201 and 202. During the nephelometric and/or fluorometric analyses, the mirrors 203 and 204 are rotated to a position shown by center lines and only the scattered and/or fluorescent light impinges upon the elements 201 and 202. In an embodiment shown in FIG. 48, the cuvette is so shaped that conventional photometric, nephelometric, and fluorometric analyses can be effected by a common light-receiving element 206. As shown in FIG. 48A, when performing conventional photometric measurements, use is made of a cuvette 45' having transparent walls perpendicular to the incident light, whereas when performing nephelometric and/or fluorometric analyses as shown in FIG. 48B, use is made of a cuvette 45" having a transparent wall inclined to the incident light.

As explained above, by effecting conventional photometric, nephelometric and/or fluorometric analyses by means of a common light-receiving element, the construction of the photometer can be much simpler.

Further in the embodiment explained above the wavelengths for particular test items are selected by the rotary filter unit 53 shown in FIGS. 7 and 8. Alternatively the optical fibers for transmitting light passing through the test liquid to the photodetector may have desired different transmission wavelengths and a given one of which may be selectively inserted in the optical path for receiving the light in dependence upon the test item to be analyzed.

What is claimed is:

1. An apparatus for delivering a certain amount of a given reagent selected from a plurality of reagents comprising:

cassette-like means holding a plurality of reagent bottles each containing more respective reagent of said plurality of reagents, said cassette-like means having a base member and upstanding vertical walls with a plurality of reagent containing bottles therein, said base member defining a path along which the bottles are conveyed;

means for detachably supporting said cassette-like means;

means for reciprocally moving the reagent bottles settled in the cassette-like in clockwise and counterclockwise rotation along said given path in order to index a desired reagent bottle to a reagent aspiration position;

means for aspirating into a probe a given amount of a selected reagent contained in the reagent bottle which is situated at the aspiration position and discharging the aspirated reagent into a reaction vessel.

2. An apparatus according to claim 1, wherein the cassette-like means comprises first and second cassette portions, reagent bottles containing reagents which have to be cooled are set in the first cassette portion, reagent bottles containing reagents which do not require cooling are set in the second cassette portion; and the apparatus further comprising means for refrigerating said first cassette portion.

3. An apparatus according to claim 1, further comprising refrigerating means for cooling the reagents contained in the reagent bottles held in the cassette-like means which is settled in the supporting means.

4. An apparatus according to claim 3, wherein said cassette-like means is so constructed that a space in which the reagent bottles are installed is substantially closed, said space being coupled to the refrigerating means so as to circulate cooling air through the cassette-like means, and the cassette-like means comprises a small opening through which the probe may be inserted into a reagent bottle.

* * * * *

UNITED STATES PATENT AND TRADEMARK OFFICE
CERTIFICATE OF CORRECTION

PATENT NO. : 4,517,160

DATED : May 14, 1985

INVENTOR(S) : Kevin GALLE, Ryoichi ORIMO, Masahiko SAKURADA, Taiichi BANNO, Sugio MANABE It is certified that error appears in the above-identified patent and that said Letters Patent is hereby corrected as shown below:

Column 21, line 32, change "more" to --one--.

Signed and Sealed this

Tenth Day of December 1985

[SEAL]

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,517,160

DATED : May 14, 1985

INVENTOR(S) : Kevin GALLE, Ryoichi ORIMO, Masahiko SAKURADA, Taiichi BANNO, Sugio MANABE It is certified that error appears in the above-identified patent and that said Letters Patent is hereby corrected as shown below:

Column 22, line 6, after "cassette-like" insert --means--.

Signed and Sealed this

Fourth Day of February 1986

[SEAL]

Attest:

Attesting Officer

DONALD J. QUIGG

Commissioner of Patents and Trademarks